United States Patent [19]
Kyle et al.

[11] Patent Number: 5,817,756
[45] Date of Patent: Oct. 6, 1998

[54] PSEUDO- AND NON-PEPTIDE BRADYKININ RECEPTOR ANTAGONISTS

[75] Inventors: Donald James Kyle, Mountain View; Babu Joseph Mavunkel; Sarjavit Chakravarty, both of Sunnyvale, all of Calif.; Zhijian Lu, Scotch Plains, N.J.

[73] Assignee: Scios Inc., Mountain View, Calif.

[21] Appl. No.: 401,595

[22] Filed: Mar. 9, 1995

Related U.S. Application Data

[63] Continuation-in-part of Ser. No. 353,426, Dec. 9, 1994, abandoned, which is a continuation-in-part of Ser. No. 281,908, Jul. 28, 1994, abandoned, which is a continuation-in-part of Ser. No. 119,341, Sep. 9, 1993, abandoned, and Ser. No. 281,907, Jul. 28, 1994, Pat. No. 5,541,286, which is a continuation-in-part of Ser. No. 118,981, Sep. 9, 1993, Pat. No. 5,444,048, and Ser. No. 281,904, Jul. 28, 1994, Pat. No. 5,686,565, which is a continuation-in-part of Ser. No. 118,550, Sep. 9, 1993, Pat. No. 5,552,383, and Ser. No. 281,906, Jul. 28, 1994, abandoned, which is a continuation-in-part of Ser. No. 118,558, Sep. 9, 1993, abandoned.

[51] Int. Cl.$^6$ ..................................................... A61K 38/06
[52] U.S. Cl. ............................ 530/331; 530/330; 514/17; 514/18
[58] Field of Search .................. 514/16, 17; 530/328, 530/329, 330, 331

[56] References Cited

U.S. PATENT DOCUMENTS

| | | | |
|---|---|---|---|
| 4,242,329 | 12/1980 | Claeson et al. | 424/177 |
| 4,483,850 | 11/1984 | Patchett et al. | 424/177 |
| 4,693,993 | 9/1987 | Stewart et al. | 514/14 |
| 4,801,613 | 1/1989 | Stewart et al. | 514/14 |
| 4,822,984 | 4/1989 | Geiger et al. | 548/252 |
| 4,923,963 | 5/1990 | Stewart et al. | 530/314 |

FOREIGN PATENT DOCUMENTS

| | | |
|---|---|---|
| 0 334 685 | 9/1989 | European Pat. Off. . |
| 0 370 453 | 5/1990 | European Pat. Off. . |
| 0 413 277 | 2/1991 | European Pat. Off. . |
| 92/18155 | 10/1992 | WIPO . |
| 92/18156 | 10/1992 | WIPO . |
| 94/08607 | 4/1994 | WIPO . |

OTHER PUBLICATIONS

Karanewsky et al., "(Phosphinyloxy)acyl amino acids inhibitors of angiotensin converting enzyme. 2. Terminal amino acid analogues of (S)–1–[6–amino–2[[hydroxy(4–phenylbutyl)phosphinyl]oxy]–1–oxohexyl]–L–proline" *J. Med. Chem.* (1990) 33(5):1459–1469.

Smith et al., "Synthesis and pharmacological activity of angiotensin converting enzyme inhibitors: N–(mercaptoacyl)–4–substituted–(S)–prolines" *J. Med. Chem.* (1988) 31(4):875–885.

Suzuki et al., "Synthesis of every kind of peptide fragments of bradykinin" *Chem. Pharm. Bull.* (1969) 17:1671–1678.

Dray et al. "Bradykinin and inflammatory pain" *TINS* (1993) 16(3):99–104.

Perkins et al., "Antinociceptive activity of the bradykinin $B_1$ and $B_2$ receptor antagonists, des–Arg$^9$, [Leu$^8$]–BK and HOE 140, in two models of persistent hyperalgesia in the rat" *Pain* (1993) 53:191–197.

Zabrocki et al., "Conformational Mimicry. 3. Synthesis and incorporation of 1,5–disubstituted tetrazole dipeptide analogues into peptides with preservation of chiral integrity: bradykinin" *J. Org. Chem.* (1992) 57(1):202–209.

Hodges et al. (eds.) *Peptides, Chemistry, Structure and Biology: Proceedings of the 13th American Peptide Symposium Jun. 20–25, 1993,* (ESCOM: Leiden, 1994), pp. 381–383.

Kyle et al., "A proposed model of bradykinin bound to the rat $B_2$ receptor and its utility for drug design" *J. Med. Chem.* (1994) 37(9):1347–1354.

*Abstracts of Papers, Part 1: 208th American Chemical Society National Meeting Aug. 21–25, 1994* 190.

Stewart, John M., "Hydroxyproline analogs of bradykinin" *J. Med. Chem.* (1974) 17(5):537–539.

Stewart, John M., "Chemistry and biologic activity of peptides related to bradykinin" *Handbook of Experimental Pharmacol.* (1979) vol. XXV Supp, Springer–Verlag Berlin Heidelberg NY.

Vavrek et al., "Smooth muscle selectivity in bradykinin analogs with multiple D–amino acid substitutions", Dept. of Biochem., University of Colorado School of Medicine, Denver, Colorado.

Rifo et al., "Bradykinin receptor antagonists used to characterize the heterogeneity of bradykinin–induced responses in rat vas deferens" *Eur. J. Pharmacol.* (1987) 142:305–312.

Zeitlin et al., "Mobilization of tissue kallikrein in inflammatory disease of the colon" Wolfson Labs, Gastrointestinal Unit, West General Hospital and Dept. of Clinical Surgery, Univ. of Edinburgh (1972) pp. 113–138.

Krapcho et al., "Angiotensin converting enzyme inhibitors. Mercaptan, carboxyalkyl dipeptide, and phosphinic acid inhibitors incorporating 4–substituted prolines" *J. Med. Chem.* (1988) 31(6):1148–1160.

Hock et al., "Hoe 140 a new potent and long acting bradykinin antagonist: in vitro studies" *Br. J. Pharmacol.* (1991) 102:769–744.

Wirth et al., "Hoe 140 a new potent and long acting bradykinin antagonist: in vivo studies" *Br. J. Pharmacol.* (1991) 102:774–777.

Pongracic et al., "A competitive kinin receptor antagonist, [DArg$^0$, Hyp$^3$, DPhe$^7$]–bradykinin, does not affect the response to nasal provocation with bradykinin" *Br. J. Pharmacol.* (1991) 31:287–294.

Higgins et al., "A study of the efficacy of the bradykinin antagonist NPC567 in rhinovirus infections in human volunteers" *Chemical Abstracts* (1991) 114:220805d.

Soler et al., "A bradykinin antagonist modifies antigen–induced airway hyper–responsiveness and airway inflammation in allergic sheep" *Am. Rev. Respir. Dis.* (1989) A327.

*Primary Examiner*—Cecilia J. Tsang
*Assistant Examiner*—David Lukton
*Attorney, Agent, or Firm*—Peter R. Shearer; Marjorie L. Jarvis

[57] ABSTRACT

The invention provides bradykinin antagonist compounds wherein many (or all) of the peptide bonds of bradykinin are eliminated to yield compounds which specifically compete with bradykinin for binding to the bradykinin receptor. More particularly, the invention relates to compounds having, in appropriate spatial arrangement, two positively charged moieties flanking a hydrophobic organic moiety and a moiety which mimics a beta turn conformation.

9 Claims, No Drawings

PSEUDO- AND NON-PEPTIDE BRADYKININ RECEPTOR ANTAGONISTS

CROSS REFERENCE TO RELATED APPLICATIONS

This application is a continuation-in-part of U.S. application Ser. No. 08/353,426 filed Dec. 9, 1994, now abandoned, which is a continuation-in-part of U.S. application Ser. No. 08/281,908 filed Jul. 28, 1994, now abandoned, which is a continuation-in-part of U.S. application Ser. No. 08/119,341 filed Sep. 9, 1993, now abandoned; and a C-I-P of U.S. application Ser. No. 08/281,907 filed Jul. 28, 1994, now U.S. Pat. No. 5,541,286 which is a continuation-in-part of U.S. application Ser. No. 08/118,981 filed Sep. 9, 1993 now U.S. Pat. No. 5,444,048 and a CIP of; U.S. application Ser. No. 08/281,904 filed Jul. 28, 1994, now U.S. Pat. No. 5,686,565, which is a continuation-in-part of U.S. application Ser. No. 08/118,550 filed Sep. 9, 1993 now U.S. Pat. No. 5,552,383, and a CIP of; U.S. application Ser. No. 08/281,906 filed Jul. 28, 1994, now abandoned, which is a continuation-in-part of U.S. application Ser. No. 08/118,558 filed Sep. 9, 1993, now abandoned.

FIELD OF THE INVENTION

This invention relates to compounds which specifically compete with native bradykinin for binding to the bradykinin $B_2$ receptor and to compounds which specifically compete with des $Arg^9$-bradykinin for the bradykinin $B_1$ receptor. The invention also relates to pharmaceutical compositions and methods for using the compounds to antagonize the effect of bradykinin in mammals, including humans.

More particularly, the invention relates to compounds having, in appropriate spatial arrangement, two positively charged moieties flanking a hydrophobic organic moiety and a moiety which mimics a beta turn conformation. These compounds interact with the bradykinin $B_2$ receptor in such a way to specifically compete with the binding of native bradykinin. Corresponding compounds which lack the positively charged moiety at one end of the molecule interact with the bradykinin $B_1$ receptor in such a way to specifically compete with the binding of des $Arg^9$-bradykinin.

BACKGROUND OF THE INVENTION

Bradykinin (BK) is a linear nonapeptide produced endogenously in humans and other mammals as a result of the activity of kallikreins, a group of proteolytic enzymes present in most tissues and body fluids, on kininogens. Once released, kinins produce many physiological responses, including pain and hyperalgesia by stimulating C- and A-fibers in the periphery. There is also considerable evidence that kinins contribute to the inflammatory response.

Native bradykinin has an amino acid sequence consisting of nine amino acids, which sequence is well known and is disclosed, for example, in published PCT application WO 92/18156, at page 6, line 17.

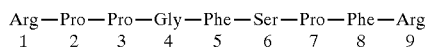

Arg—Pro—Pro—Gly—Phe—Ser—Pro—Phe—Arg
1    2    3    4    5    6    7    8    9

Bradykinin, and its physiologically important related peptides kalladin (Lys-bradykinin) and Met-Lys-bradykinin, exhibit physiological actions which qualify them as mediators of inflammatory reactions, hypotensive states, and pain. Bradykinin is overproduced in pathological conditions such as septic shock, anaphylaxis, rhinitis, asthma, inflammatory bowel disease, and certain other conditions including acute pancreatitis, post-gastrectomy dumping syndrome, carcinoid syndrome, migraine, and angioneurotic edema. The production of bradykinin from the plasma results in pain at the site of the pathological condition, and the overproduction intensifies the pain directly or via bradykinin-induced activation of the arachidonic acid pathway which produces prostaglandins and leukotrienes, the more distal and actual mediators of inflammation.

In addition to its proinflammatory effects, bradykinin is a vasodilator. Because of its concomitant ability to lower blood pressure, bradykinin has been implicated in the pathogenesis of several shock syndromes, particularly septic or endotoxic shock. Bradykinin is also a potent bronchoconstrictor in animals and asthmatic subjects and it has been implicated as a contributor to the pathogenesis of airway inflammatory conditions such as allergic asthma and rhinitis.

As a result of the implication that increased levels of bradykinin may play a part in a number of pathological conditions, considerable research has been aimed toward the derivation of bradykinin receptor antagonists as potential therapeutic agents. A bradykinin receptor antagonist is expected to possess a number of desirable biological effects in the treatment, for example, of pain and inflammation, septic shock, airway disorders such as asthma, burn pain, pancreatitis, angioedema, certain nervous system disorders, chronic inflammation such as rheumatoid arthritis and inflammatory bowel disease, rhinitis, and allergy.

Several non-peptide, non-specific and non-selective antagonists of one or more of the biological activities of bradykinin have been described among compounds as diverse as analgesics and anti-inflammatory substances, which act via the prostaglandin system and not directly on bradykinin receptors. These are antihistamines, bradykinin-antibodies, benzodiazepine derivatives, high molecular weight ethylene oxide polymers, gallic acid esters, and serotonin inhibitors. None of these compounds or classes of compounds specifically inhibit the effects of bradykinin.

Heptyl esters of various amino acid-containing substances, such as single basic amino acids the dipeptide Phe-Gly, and analogs of C-terminal peptide fragments of bradykinin (i.e., Pro-Phe-Arg) have been reported as anti-bradykinin substances. When tested in bradykinin assay systems, they prove to be weak partial agonists/antagonists, depending on the dose, with little specificity for inhibiting bradykinin action.

Several research groups have prepared bradykinin receptor antagonists. The first antagonists of bradykinin were discovered by Stewart and Vavrek. U.S. Pat. Nos. 4,801,613 and 4,693,993 (which references are incorporated in their entirety herein) disclose a series of bradykinin antagonists wherein the L-Pro at the 7-position of the peptide hormone bradykinin or other substituted analogs of bradykinin is substituted with an aromatic amino acid of the D-configuration which converts bradykinin agonists into bradykinin antagonists. The specific L-Pro substitutions are selected from the group consisting of D-Nal, D-PNF, D-Phe, D-Tyr, D-Pal, D-OMT, D-Thi, D-Ala, D-Trp, D-His, D-Homo-Phe, D-Phe, pCl-D-Phe (CDF), D-Phg, D-Val, D-Ile, D-Leu, and MDY. Typically, these bradykinin antagonist peptides had $K_i$ values in the range of 20–80 nM in guinea pig ileum (Stewart, et al., In *Bradykinin Antagonists* (1991) Burch, R. M., Marcel Dekker, New York).

Subsequently, several classes of bradykinin antagonist peptides with 600–1000-fold greater potency in the guinea pig ileum preparation have been disclosed. Published European Patent Application No. 0 413 277 A1 to Hoechst A. G. discloses bradykinin antagonists containing the aromatic amino acid D-Phe at position 7 but containing unnatural amino acids at position 8 which impart increased potency.

Published European Patent Application No. 0 370 453 A2 to Hoechst A. G. discloses bradykinin antagonists containing a D-amino acid (D-Tic) at position 7.

A more recent series of bradykinin receptor antagonist peptides lacks the D-aromatic amino acid at position 7 which was believed to be critical to the activity of the earlier described antagonists of the endogenous neuropeptide. As described in published PCT application WO 92/18156 and WO 92/18155 (which references are incorporated in their entirety herein) this group of compounds have a general bradykinin antagonist structure wherein the L-Pro at position 7 is substituted with hydroxyproline ether and thioether derivatives (termed D-Hype) and the L-Phe at position 8 can additionally be substituted with hydroxyproline ethers and thioethers derivatives (Hype), Tic or Oic.

The bradykinin antagonist peptides referred to above exert their activity by blocking the bradykinin $B_2$ receptor. A second bradykinin receptor, the $B_1$ receptor, is not expressed to any significant degree in healthy tissue, but its expression is upregulated during persistent inflammatory hyperalgesia. This receptor is activated by des $Arg^9$-kalladin and des $Arg^9$-bradykinin, a proteolytic degradation product of bradykinin. It is believed to play an important role in the maintenance of hyperalgesia in chronic inflammatory conditions (Dray, A. and Perkins, M., *TINS* (1993) 16(3) :99–103). [Des-$Arg^9$] analogs of bradykinin $B_2$ receptor antagonist peptides of the type described above, bind to the $B_1$ receptor and have been shown to reverse or prevent hyperalgesia in animal models of persistent inflammatory hyperalgesia, whereas the corresponding $B_2$ receptor antagonists were ineffective or weakly active in these models (Perkins et al., *Pain* (1993) 53:191–197).

One limitation of the bradykinin antagonist peptides known to date is the necessity for parenteral administration. Due to the peptidic nature of the compounds, they are unlikely to be orally active. Further, peptides in general tend to have a relatively short duration of action as a consequence of their rapid metabolic degradation. As a result, non-peptide or pseudopeptide bradykinin receptor antagonists that lack the limitations of a peptide offer meaningful therapeutic advantages.

SUMMARY OF THE INVENTION

The present invention resides in the discovery that the novel pseudopeptide compounds identified below, are potent bradykinin receptor antagonists. The compounds are useful in the treatment of various diseases including inflammatory disorders, asthma, septic shock, and burn pain. Included in the invention are pharmaceutical compositions containing the inventive compounds and methods of using the compounds as bradykinin receptor antagonists.

The compounds of the invention which interact with the $B_2$ receptors have the formula:

X-Y-Z wherein,

X is a moiety having a net positive charge;

Y is a hydrophobic organic moiety having a nitrogen atom at the X-Y junction, a carbonyl group at the Y-Z junction, an atomic volume in the range of 135 $Å^3$ to 300 $Å^3$, and an end-to-end distance between the flanking nitrogen and carbonyl atoms of about 5.0 Å±1.5 Å;

Z is an arrangement of atoms which inherently adopt a beta turn conformation and has a positive charge near the distal end.

Preferred compounds of the formula X-Y-Z are those which have a binding affinity constant (Ki) of less than 500 nm, more preferably less than 100 nm, for membrane bound human bradykinin $B_2$ receptor, using the assay procedure described herein.

In another embodiment, the invention relates to pseudopeptide compounds capable of binding to the bradykinin $B_1$ receptor. These compounds, because of their ability to block $B_1$ receptor mediated hyperalgesia, are useful in the treatment of conditions associated with chronic inflammation. In particular, these compounds have the same structure as that set forth for the $B_2$ receptor antagonists described above with the exception that they lack the positively charged moiety at the distal end of the Z group.

The compounds of the invention have numerous advantages over conventional peptide bradykinin agonists. The most salient advantage is the elimination of many (or all) of the amide bonds from the bradykinin-like structure. Reduction or elimination of the peptide nature of the compounds leads to compounds having an increased duration of action. The compounds of the invention are longer lasting and have a wider range of administration modes than conventional peptide bradykinin antagonists (e.g., do not necessarily require parenteral administration, may possibly be orally active). The compounds of the invention are also less expensive to prepare than peptide bradykinin antagonists.

Another embodiment of the invention involves a pharmaceutical composition useful as a bradykinin receptor antagonist comprising a pharmaceutical carrier and an effective amount of the compound of the invention. The invention also involves a process for antagonizing bradykinin receptor activity in mammals which comprises administering to a subject an effective amount of the novel compound to antagonize bradykinin receptor activity.

A further embodiment involves a pharmaceutical preparation for treating local pain and inflammation from burns, wounds, cuts, rashes and other such trauma, and pathological conditions caused by the production of bradykinin or related kinins by an animal which comprises administering an effective amount of the novel compound sufficient to antagonize bradykinin with a suitable pharmaceutical carrier. Another aspect of this invention involves a process for treating local pain and inflammation which comprises administering an effective amount of the pharmaceutical preparation to an animal in need thereof.

DETAILED DESCRIPTION OF THE INVENTION

The compounds of the invention which are capable of specifically competing with native bradykinin for binding to the bradykinin $B_2$ receptor have the following structure:

X-Y-Z wherein,

X is a moiety having a net positive charge selected from the group comprising a positively charged amino acid and an organic group;

Y is a hydrophobic organic moiety having the following characteristics:

a. a nitrogen atom at the X-Y junction;

b. a carbonyl group at the Y-Z junction;

c. the hydrophobic organic moiety between the nitrogen atom and the carbonyl group is selected from the group consisting of a carbocyclic, heterocyclic and a linear organic moiety;

d. an atomic volume in the range of 135 Å³ to 300 Å³;

e. an allowed conformation such that an end-to-end distance between the flanking nitrogen and carbonyl atoms is about 5.0 Å±1.5 Å;

f. with the proviso that Y cannot consist of naturally occurring amino acids;

Z is an arrangement of atoms which inherently adopt a beta turn conformation and has a positive charge near the distal end;

and pharmaceutically acceptable salts thereof.

The compounds of the invention which are capable of specifically competing with des Arg⁹-bradykinin for binding to the bradykinin B₁ receptor have the following structure:

X-Y-Z' wherein, X and Y are as defined above and Z' is an arrangement of atoms which inherently adopt a beta turn conformation and which lacks a positive charge near the distal end; and pharmaceutically acceptable salts thereof.

A. Preferred X Moieties

X is a moiety having a net positive charge. Preferably X comprises a positively charged amino acid or an organic group. Alternatively, X can comprise both a positively charged amino acid and an organic group. When X comprises a positively charged amino acid, it preferably is a mono-, di- or tri-peptide independently selected from the group consisting of the L- and D- isomers of Arg, Gln, Asn, Lys, Sar, N-ε-acetyl-Lys, $N^G$-p-tosyl-Arg-$N^G$-nitro-Arg, acetyl-Arg, and citrulline. Most preferably X is D-Arg-Arg. X may also comprise a non-natural amino acid which acts as an arginine mimetic. Useful arginine mimetics are disclosed, for example, in *Biochemistry* (1975) 14(23):5194–5195 and *Pharmazie* (1974) 29(1):12–15. When the group Y is as described in Formula 2, below, then X may also preferably by a tripeptide (I-II-III) in which amino acids I and II are independently selected from the group consisting of the L- and D-isomers of Arg, Gln, Asn, Lys, Sar, N-ε-acetyl-Lys, $N^G$-p-tosyl-Arg$N^G$-nitro-Arg, acetyl-Arg and citruline ,and amino acid III is selected from the group consisting of Pro, 4Hyp and Oic. A preferred tripeptide representing X, when Y is described in Formula 2, is D-Arg-Arg-Pro.

When X is an organic moiety it can include, but is not limited to, triazole, 8-guanidinooctanoic acids, 10-aminodecanoic acids and N-[(5-guanidino)pentyl]-Arg. In these organic moieties the alkyl bridge may be substituted, branched, straight, cyclic, saturated or unsaturated.

B. Preferred Y Moieties

Y is a hydrophobic organic moiety having the following characteristics:

a. a nitrogen atom at the X-Y junction;

b. a carbonyl group at the Y-Z junction;

c. the hydrophobic organic moiety between the nitrogen atom and the carbonyl group is selected from the group consisting of a carbocyclic, heterocyclic and a linear organic moiety;

d. an atomic volume in the range of 135 Å³ to 300 Å³;

e. an allowed conformation such that an end-to-end distance between the flanking nitrogen and carbonyl atoms is about 5.0 Å±1.5 Å;

f. with the proviso that Y cannot consist of naturally occurring amino acids.

The hydrophobic organic moiety Y must satisfy at least a two part criterion. The first criteria is related to a conformationally allowed end-to-end length of the isolated moiety and the second criteria is related to atomic volume.

When considered in isolation from the complete molecule (X-Y-Z), Y must be able to adopt an N-terminal to C-terminal distance of about 5.0 Å±1.5 Å. The end-to-end distance between the flanking nitrogen and carbonyl atoms of about 5.0 Å±1.5 Å is achieved via either inherent flexibility or inherent rigidity. This geometric constraint might be a function of some inherent structural rigidity imparted, for example, by unsaturation or cyclization. Alternatively, this preferred geometry might be attainable geometry in which the fragment Y is able to satisfy the end-to-end distance via inherently flexible conformational changes which would be allowed on the basis of a Boltzmann distribution of conformational states at room temperature.

Further, an acceptable Y has an atomic volume of not less than 135 Å³ and not greater than 300 Å³ as determined by the numerical integration method of Pearlstein, R. A. (Thesis, Department of Macromolecular Science, Case Western Reserve University, Cleveland, Ohio, 1983). Preferably, Y is selected from the group consisting of carbocyclic, heterocyclic, polycyclic and linear (saturated and unsaturated) organic molecules. Y cannot comprise a natural amino acid. Y moieties which do not satisfy both parts of the criterion, length and volume, are not acceptable as Y in the compounds of the invention.

Several of the hydrophobic spacer groups (Y) specifically defined by this invention include, but are not limited to:

1,2-benzo-4-keto-3,8-diazaspiro[4.5]decan-3-alkanoic acids, 1,2,3,4-tetrahydro-9H-pyrido[3,4-b]indol-9-alkanoic acids (β-carboline-alkanoic acids), 1,2,3,4-tetrahydro-5H-pyrido[4,3-b]indol-5-alkanoic acids (β-carboline-alkanoic acids), amino-2-quinolinon-1-alkanoic acids, amino-6-(5H)phenanthridinon-5-alkanoic acids, 1-(4-piperidinyl)-2-benzimidazolon-3-alkanoic acids, N-(aminophenyl)-N-benzoylglycine-N-alkanoic acids, ω-aminoalkanoic acids, substituted ω-aminoalkanoic acids, olefinic ω-aminoalkenoic acids, and 4-keto-1,3,8-triazaspiro[4.5]decan-3-alkanoic acids.

In various embodiments of the invention, the Y group can have any of the formulae selected from Formula 1, Formula 2 and Formula 3 below:

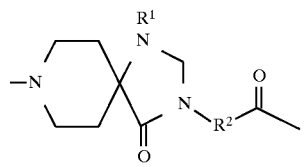

Formula 1 wherein R¹ is selected from the group consisting of a substituted or unsubstituted aryl group, a straight, branched, saturated or unsaturated lower alkyl chain of 1 to 6 carbon atoms, and a cycloalkyl or cycloalkylmethyl in which the cycloalkyl ring comprises 3 to 6 carbon atoms; and R² is a saturated or unsaturated alkylene bridge consisting of 1 to 8 carbon atoms optionally substituted with a benzyl or naphthyl group or in which one of the carbon atoms of the bridge is disubstituted to form a cycloalkyl ring consisting of 3 to 6 carbon atoms.

In Formula 1, $R^1$ is preferably selected from the group consisting of a cyclohexyl, phenyl, naphthyl, benzyl or naphthylmethyl group optionally substituted with a $C_1$ to $C_2$ lower alkyl group, a $C_1$ to $C_4$ alkoxy group or a halogen. More preferably, $R^1$ is selected from the group consisting of phenyl, 4-methylphenyl, 4-methoxyphenyl, 4-fluorophenyl, 4-chlorophenyl, benzyl, 1-naphthyl, 2-naphthyl, cyclohexyl, cyclohexylmethyl, n-propyl, n-pentyl and neopentyl. Most preferably, $R^1$ is selected from the group consisting of phenyl, 4-methylphenyl, cyclohexyl, cyclohexylmethyl and n-propyl.

In Formula 1, $R^2$ is preferably a saturated or unsaturated alkylene bridging group consisting of 1 to 8 carbon atoms optionally substituted with a benzyl or naphthyl group. More preferably, $R^2$ is a saturated or unsaturated alkylene bridging group consisting of 1 to 4 carbon atoms. Most preferably, $R^2$ is $(CH_2)_x$ wherein x is an integer from 1 to 4.

Formula 2

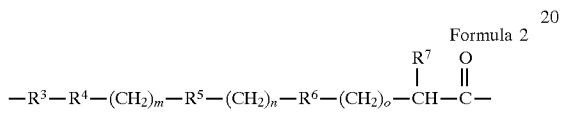

wherein $R^3$ is a direct bond or is selected from the group consisting of 2-pyrrolidinyl, Pro, 4Hyp, Oic, dehydroPro, Tic, Aoc, L-azetidine-2-carboxylic acid, Eac, Gly, Thz, and Aib; $R^4$ is selected from the group consisting of a direct bond and an imino (—NH—) group; $R^5$ and $R^6$ are independently selected from the group consisting of a direct bond, a $C_3$ to $C_8$ carbocycle and a $C_2$ to $C_{18}$ monoolefin or a $C_4$ to $C_{18}$ polyolefin containing 2 to 5 double bonds which may optionally be incorporated into a cyclic system; $R^7$ is selected from the group consisting of hydrogen, hydroxymethyl, $C_1$ to $C_6$ alkyl, benzyl, thiophenylmethyl and furanylmethyl; and m, n, and o are independently an integer from 0 through 12, with the proviso that their total does not exceed 12.

In Formula 2, $R^3$ is preferably selected from the group consisting of 2-pyrrolidinyl, Pro, 4Hyp and Oic. More preferably, $R^3$ is selected from 2-pyrrolidinyl and Oic.

Preferred Y groups of Formula 2 include those wherein $R^5$ is selected from the group consisting of a direct bond, a $C_3$ to $C_8$ carbocycle, and a $C_2$ to $C_{18}$ monoolefin or $C_4$ to $C_{18}$ polyolefin containing 2 to 5 double bonds which may optionally be incorporated into a cyclic system; $R^6$ is selected from the group consisting of a direct bond and a $C_2$ to $C_{18}$ monoolefin; $R^7$ is selected from the group consisting of hydrogen and benzyl; and m, n, and o are independently an integer from 0 to 6.

Preferred cyclic systems incorporated into $R^5$ and $R^6$ include:

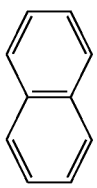

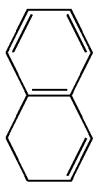

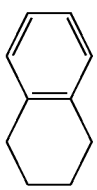

Preferred Y groups of Formula 2 in which $R^3$ is a direct bond include, but are not limited to:

4-amino-2-butenoyl;

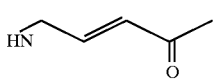

3-[2-(aminomethyl)phenyl]-2-propenoyl;

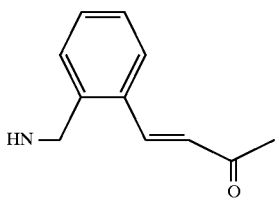

3-[2-(aminomethyl)phenyl]-2-propanoyl;

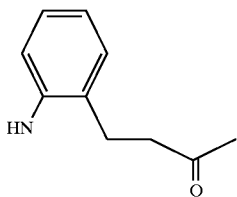

3-[3-(aminomethyl)phenyl]-2-propenoyl;

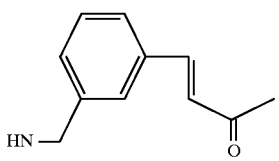

-continued

3-[3-(aminomethyl)penyl]-2-propanoyl;

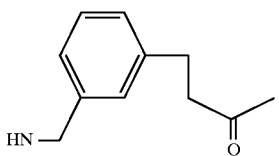

4-[2-(aminomethyl)phenyl]-3-butenoyl;

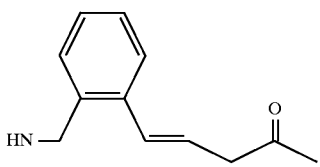

3-[2-(aminoethyl)phenyl]-2-propenoyl;

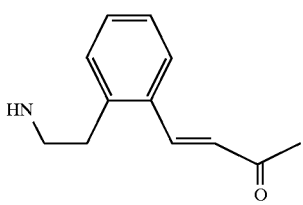

6-amino-4,5-(1,2-cyclohexyl)-2-hexenoyl;

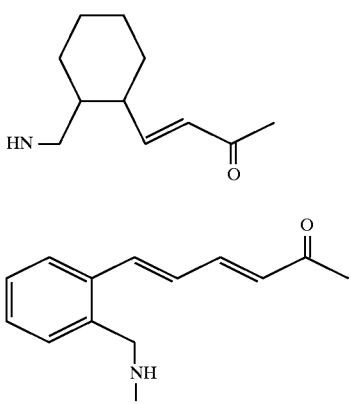

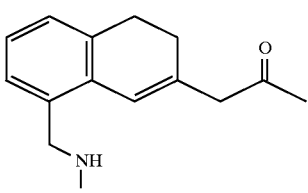

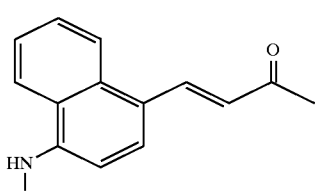

-continued

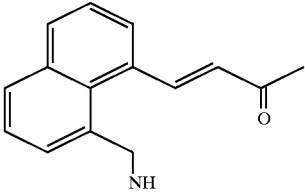

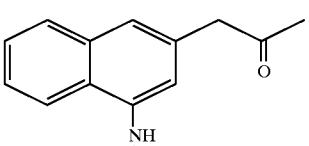

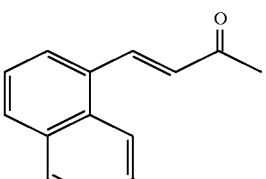

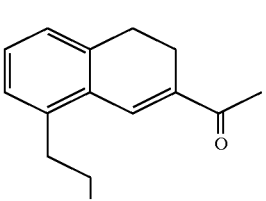

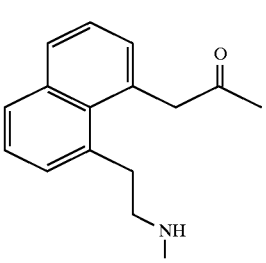

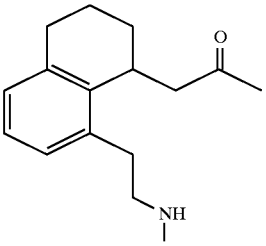

$$\text{—NH—(CH}_2)_m\text{—R}^5\text{—(CH}_2)_n\text{—R}^6\text{—(CH}_2)_o\text{—}\overset{\overset{\displaystyle O}{\|}}{C}\text{—} \quad \text{Formula 3}$$

wherein $R^5$, $R^6$, m, n, and o are as previously defined for Formula 2.

Exemplary of other hydrophobic spacer groups (Y), which satisfy the criteria set forth above for Y are the following, which are intended to be illustrative only and not to limit the scope of the invention:

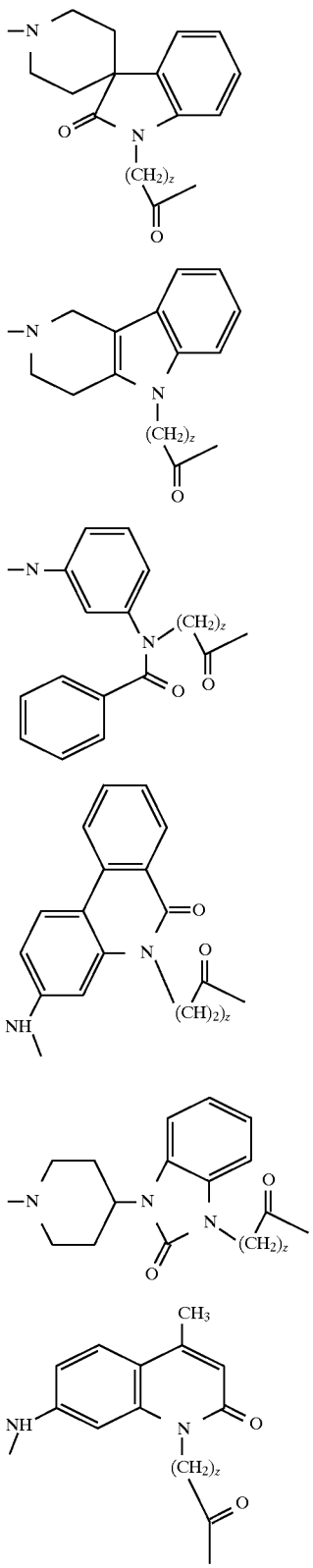

In the above formulae, z is an integer from 1 to 3.

Examples of routes of synthesis of protected hydrophobic spacer moieties (Y) described above, which are suitable for incorporation into the pseudopeptide or non-peptide bradykinin antagonists of the invention by known coupling techniques, are shown below in Schemes I–XIV.

For incorporation of these aminoacyl groups into the bradykinin antagonists of the invention it is necessary to protect the amino functionality with, for example, Boc (tert-butoxycarbonyl) or FMOC (9-fluorenylmethoxycarbonyl) groups. The required N-protected amino acids are generally derived by a sequence that involves addition of an amine-protecting group to an ester of the amino acid spacer group, followed by hydrolysis of the ester. In most instances, requisite esters are obtained by alkylation of an amide or amide-like precursor (see Schemes I–V) with an alkyl haloalkanoate. Following acylation with a suitable protecting group, the protected aminoester is hydrolyzed to the protected amino acid. The amide or amide-like starting materials have been described previously, are commercially available or are prepared by conventional chemical synthetic procedures that are well known to those skilled in the art.

As shown in Scheme I, bis-alkylation of oxindole with bis-chloroethylmethylamine affords a spiro-piperidine which is alkylated with methyl bromoacetate. Sequential N-demethylation, Boc protection and ester hydrolysis of the derived acetate affords N-Boc-1,2-benzo-4-keto-3,8-diazaspiro[4.5]decan-3-acetic acid.

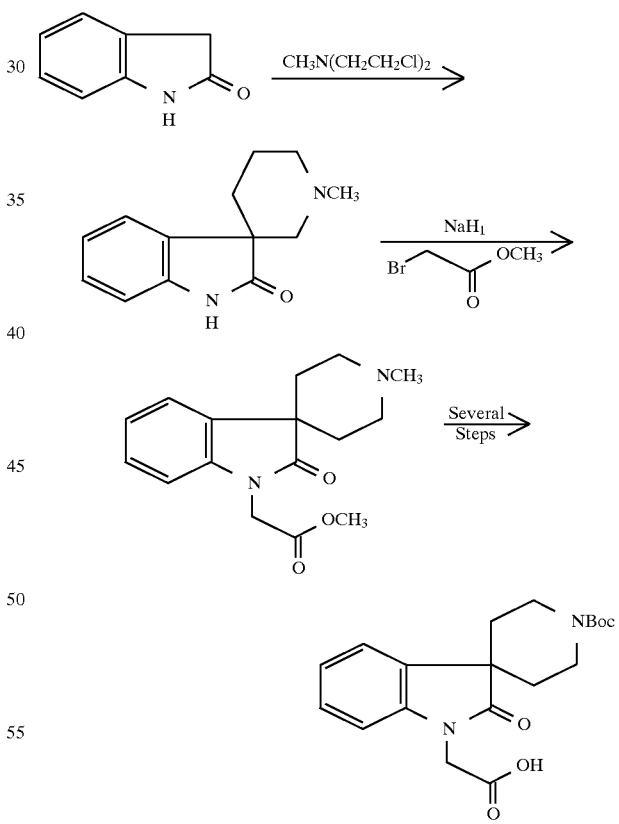

Boc-protected 1,2,3,4-tetrahydro-9H-pyrido[3,4-b]indol-9-alkanoic acids are derived from 1,2,3,4-tetrahydro-9H-pyrido[3,4- b]indole (1,2,3,4-tetrahydro-β-carboline (Aldrich Chemical Company, Milwaukee, Wis.) by similar Boc-protection, followed by alkylation with ethyl bromoacetate or ethyl 3-bromopropionate and ester hydrolysis.

As illustrated in Scheme II, N-Boc-1,2,3,4-tetrahydro-5H-pyrido [4,3-b]indol-9-acetic acid is derived from N-carbethoxy 4-piperidone and phenylhydrazine condensation in a Fischer indole synthesis, followed by carbethoxyalkylation, Boc protection and ester hydrolysis.

Scheme II

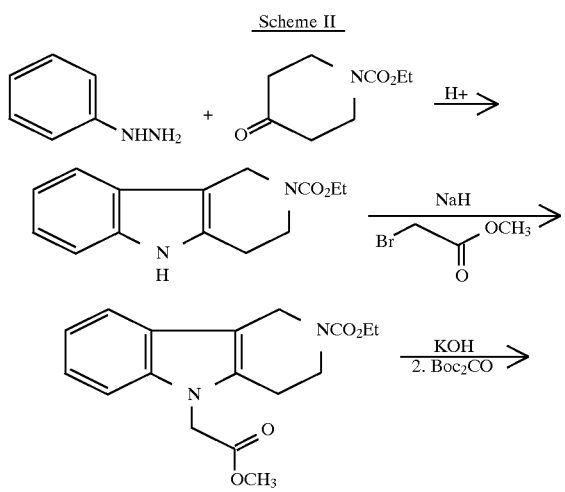

7-(9-FMOC-amino)-4-methyl-2-quinolion-1-acetic acid is derived from 7-amino-4-methyl-2-quinolinone (Chilin et al., *J. Org. Chem.* (1991) 56:980–983) in a related alkylation, N-protection, hydrolysis sequence as illustrated in Scheme III.

Scheme III

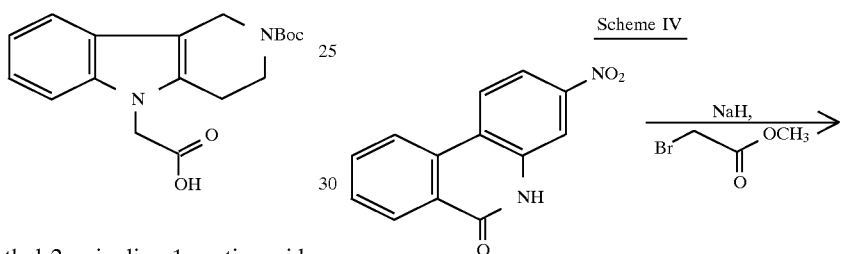

-continued

Scheme III

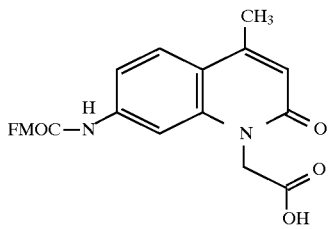

Boc-protected 3-amino-6(5H)phenanthridinon-6-acetic acid is prepared from 3-nitro-6(5H)phenanthridinon (Rare Chemical Collection, Aldrich Chemical Company, Milwaukee, Wis.) by methyl bromoacetate alkylation, nitro group reduction, amine protection and ester hydrolysis as outlined in Scheme IV.

Scheme IV

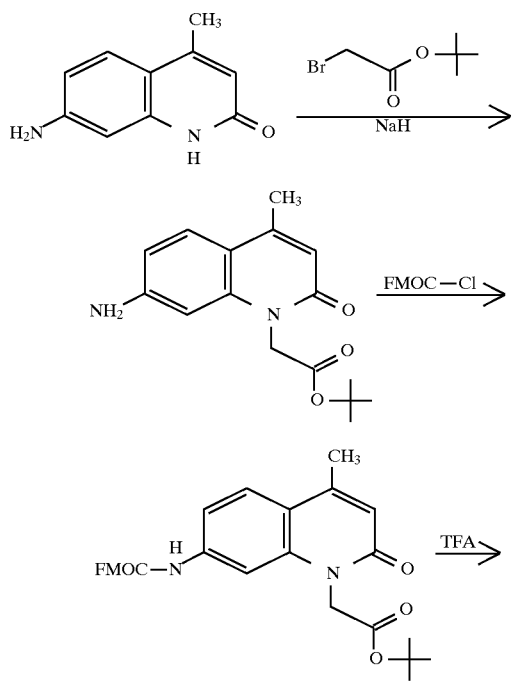

As shown in Scheme V, a similar procedure is employed to prepare Boc-protected N-aminophenyl-N-benzoylglycine-N-acetic acid.

Scheme V

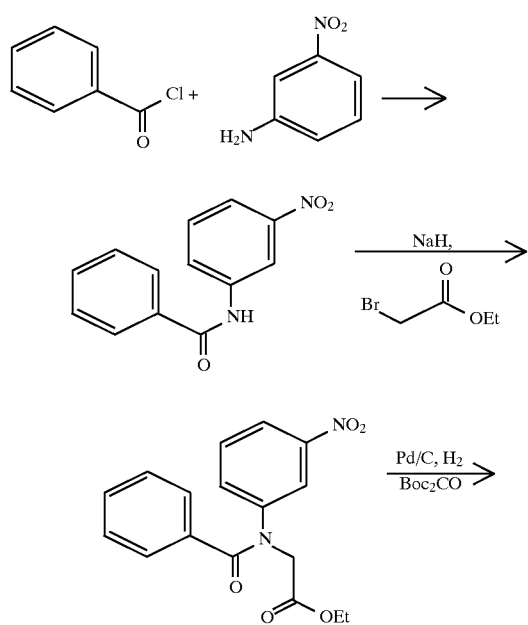

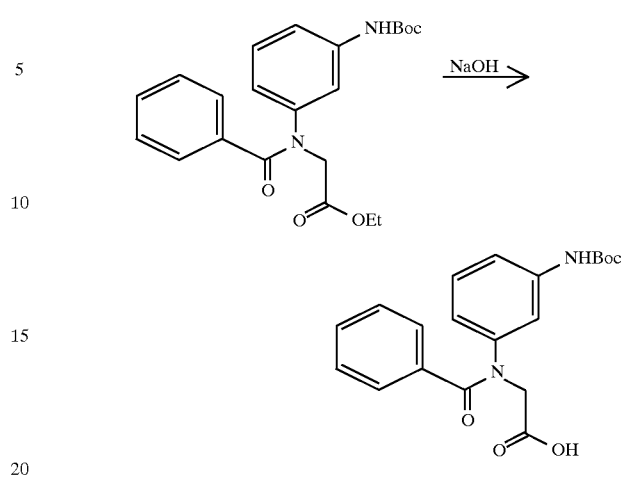

Boc-protected 1-(4-piperidinyl)-2-benzimidazolinon-3-acetic acid is derived from 1-(4-piperidinyl)-2-benzimidazolinone (Aldrich Chemical Company, Milwaukee, Wis.) by alkylation with ethyl iodoacetate followed by Boc acylation and ester hydrolysis.

Boc-protected ω-alkanoic acids, as well as their substituted and olefinic derivatives, and substituted 4-keto-1,3,8-triazaspiro[4.5]decan-3-alkanoic acids are obtained as described in co-owned, copending U.S. patent applications.

Scheme VI
Preparation of protected hydrophobic spacer group (Y) of Formula 1:

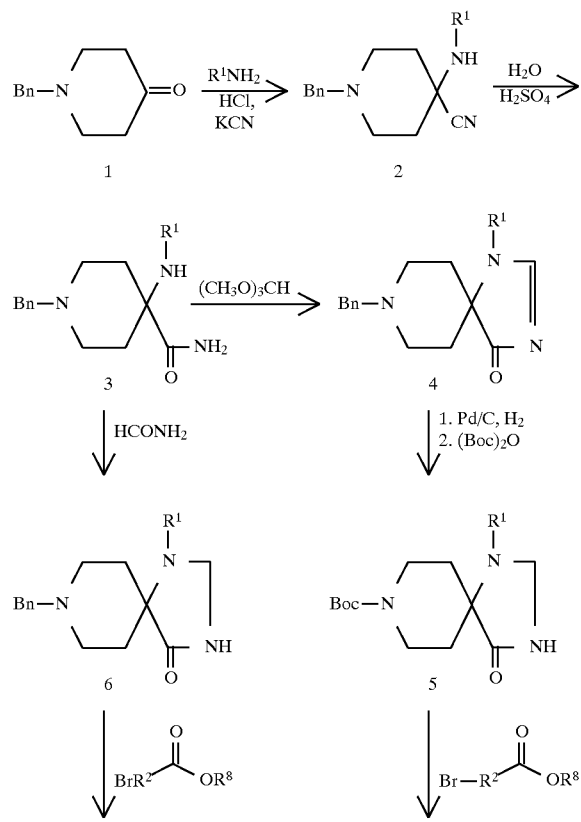

-continued
Scheme VI
Preparation of protected hydrophobic spacer group (Y) of Formula 1:

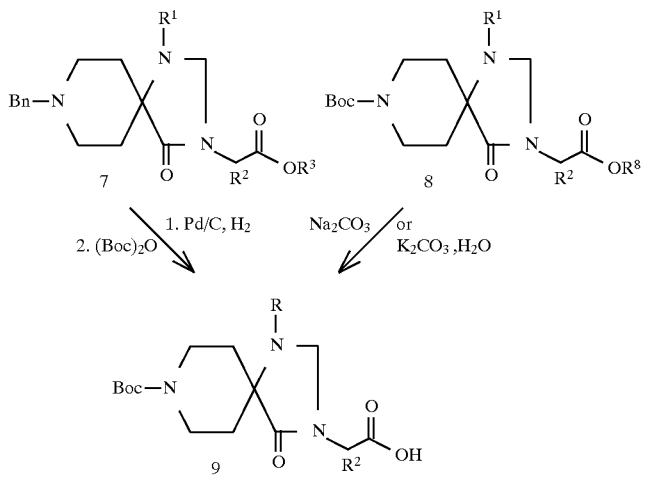

wherein $R^1$ and $R^2$ are as defined for Formula 1; $R^8$ is $CH_3$, $C_2H_5$ or benzyl (Bn).

Preparation of an N-Boc protected substituted ω-aminoalkanoic acid for introduction of a hydrophobic spacer (Y) of Formula 2 (wherein $R^4$ is an imino group) into the pseudopeptides of this invention is illustrated by the synthesis of N-Boc-5-amino-2-benzyl-3-pentenoic acid (10) as outlined in Scheme VII (in which $B_n$ represents benzyl).

Scheme VII

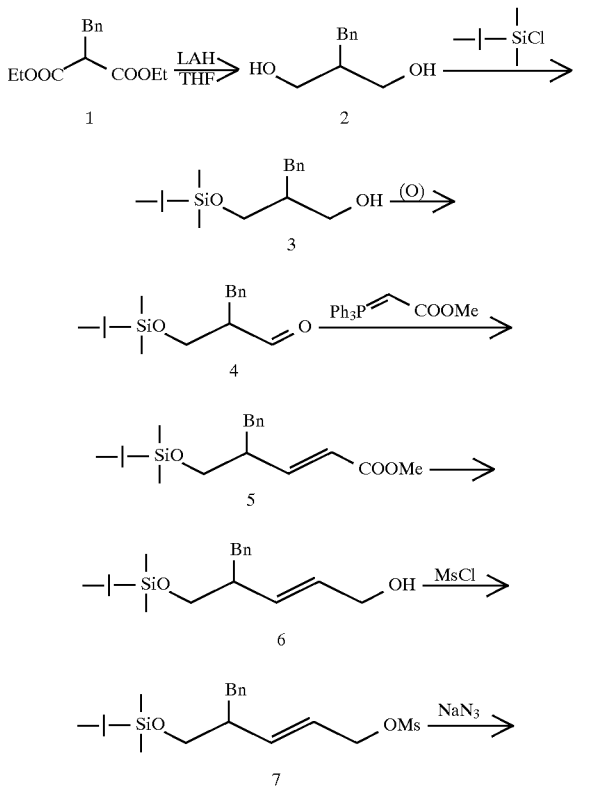

-continued
Scheme VII

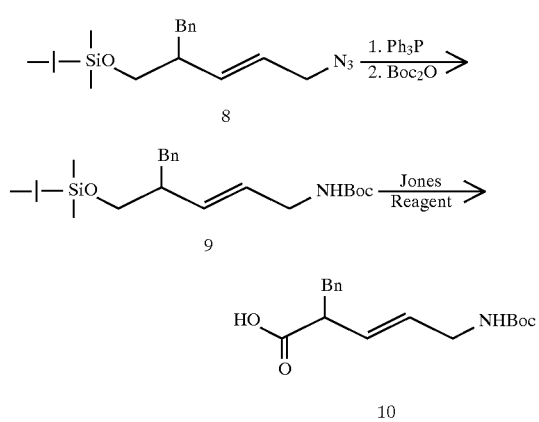

Accordingly, diethyl benzylmalonate (1) is reduced with lithium aluminum hydride to afford 2-benzyl-1,3-propanediol (2) which is treated with an equimolar amount of tert-butyldimethylsilyl chloride to give the monoprotected alcohol 3. Swern (dimethylsulfoxide/oxalyl chloride) oxidation of 3 provides the aldehyde 4 which is condensed with the Wittig reagent methyl (triphenylphosphonylidene) acetate to give 6. Conversion of the alcohol 6 to the mesylate 7 followed by azide displacement affords 8 which is sequentially reduced and Boc protected to give 9. Jones oxidation of the tert-butyldimethylsilyl ether 9 provides the Boc protected substituted ω-aminoalkenoic acid 10.

By alteration of the benzyl substituent of the malonate starting material the group $R^7$ of the general structure of Formula 2 may be varied. Modification of the reagent employed for Wittig condensation with the aldehyde, e.g., 4, enables variation of $R^5$, $R^6$, m, n, and o of the aminoalkenoyl group of Formula 2 that is introduced into the pseudopeptides of this invention.

The general method utilized to prepare mono- and polyolefinic substituted ω-(2-pyrrolidinyl)alkenoic acids for introduction of the fragments wherein $R^3$ is 2-pyrrolidinyl and the remainder of the Y group is an alkenoyl group into the pseudopeptides of this invention is illustrated by the synthesis of (2S-2S-benzyl-7-(2S-pyrrolidinyl)-6-heptenoic acid (18) as outlined in Scheme VIII. Substituted ω-(2-pyrrolidinyl)alkanoic acids 19 are obtained by catalytic hydrogenation of olefinic precursors as shown in Scheme VIII (in which $B_n$ represents a benzyl group).

Scheme VIII

The initial step in this sequence involves conversion of Boc-protected L(S)-proline (11) to 2-pyrrolidinecarboxaldehyde (13) via Boc-protected N-methoxyl-N-methyl-L-prolinamide (12) according to previously described methodology [Fehrentz, J. A. and Castro, B., *Synthesis* (1983) 676–678; Hocart, S. J., et al., *J. Med. Chem.* (1988) 31:1920–1824; Nahm, S. and Weinreb, S. M., *Tet. Lettr.* (1981) 22:8315–3818]. Condensation of 13 with the Wittig reagent derived from 6-bromohexanoic acid and triphenylphosphine according to the general method of Corey, H. S., Jr. et al. [*J. Am. Chem. Soc.* (1964) 86: 1884] produced Boc-protected 7-(2-pyrrolidinyl)-6-heptenoic acid (14) which is stereoselectively benzylated via the chiral amide 15 to produce 16 according to a previously described general procedure [Mavunkel, B. J., et al., *Tet. Lettr.* (1993) 14:2225]. Alcoholysis of the amide with benzyl alcohol gives the ester 17 which is hydrolyzed to 18 according to the procedure of Evans, D. R., et al. [*J. Org. Chem.* (1985) 50:1930–1835]. Hydrogenation of 18 results in the saturated benzyl-substituted ω-(2-pyrrolidinyl)alkanoic acid 19.

Preparation of hydrophobic spacer groups (Y) of Formula 3 for incorporation into the bradykinin antagonists of the invention is illustrated by Schemes IX to XIV.

Scheme IX

N-Boc-protected 3-[2-(aminomethyl)phenyl]-2-propenoic acid (Compound 1) and N-Boc-protected 3-[2(aminomethyl)phenyl]-2-propanoic acid (Compound 2) were prepared via the following scheme:

Scheme IX -continued
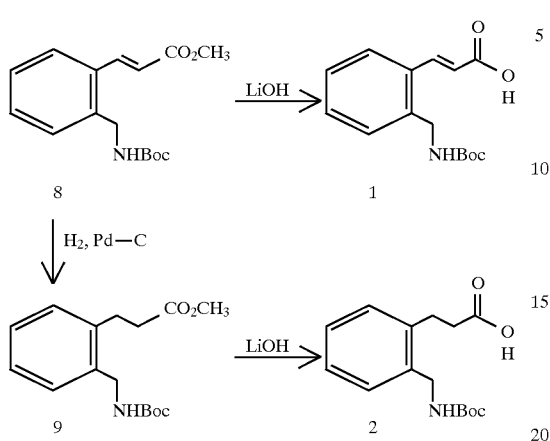
Scheme X
N-Boc-protected 3-[3-(aminomethyl)phenyl]-2-propenoic acid (Compound 3) and 3-[3-(aminomethyl)phenyl]-2-propanoic acid (Compound 4) were prepared by the following scheme:
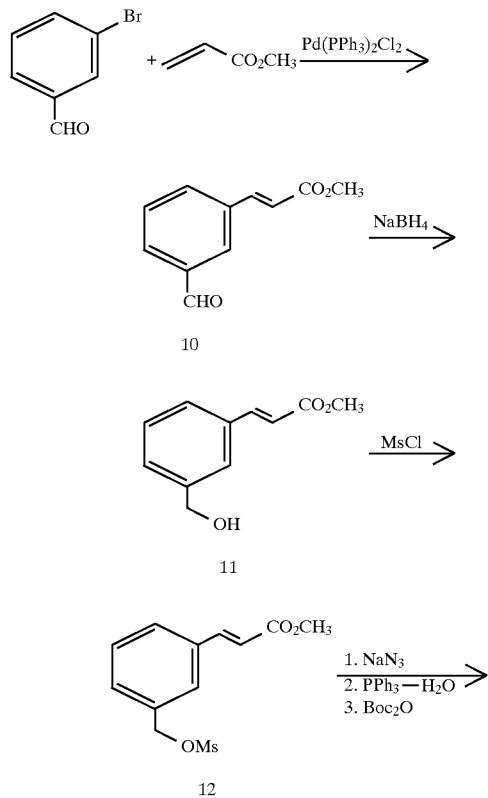
Scheme X -continued
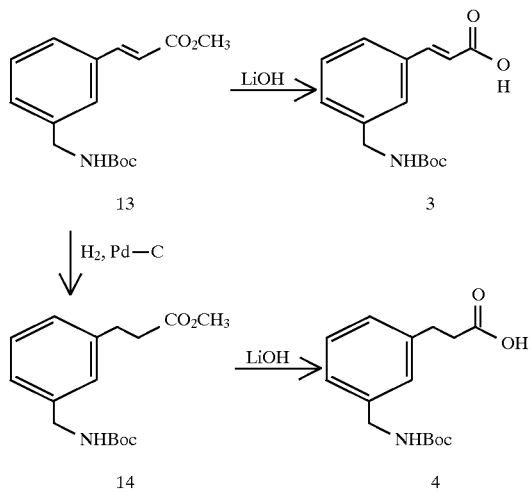
Scheme XI
N-Boc-protected 4-[2-(aminomethyl)phenyl]-3-butenoic acid (Compound 5) was prepared via the following scheme:
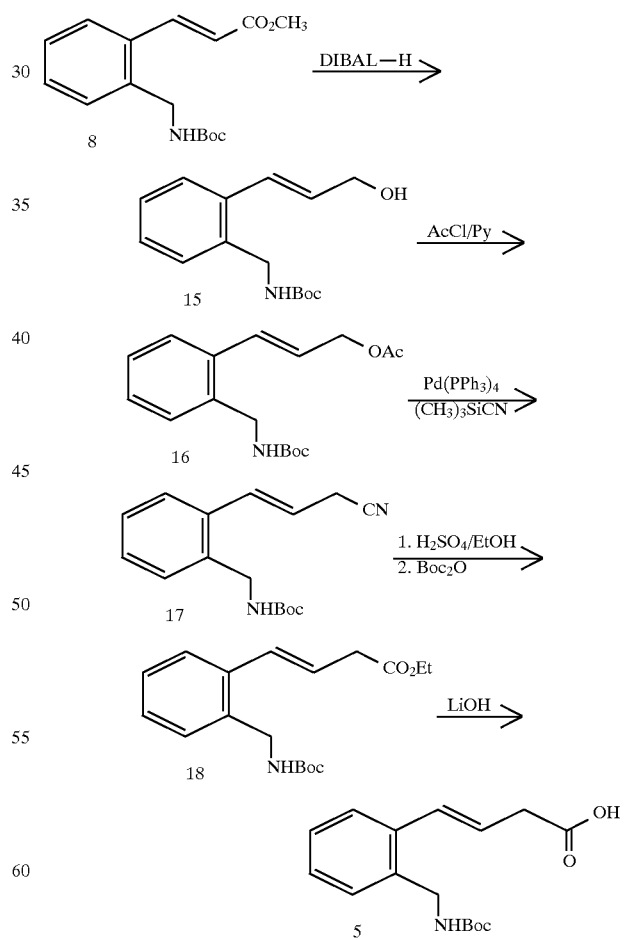

Scheme XII

N-Boc protected 2-[(2-aminoethyl)phenyl]propenoic acid (Compound 23) was prepared via the following scheme:

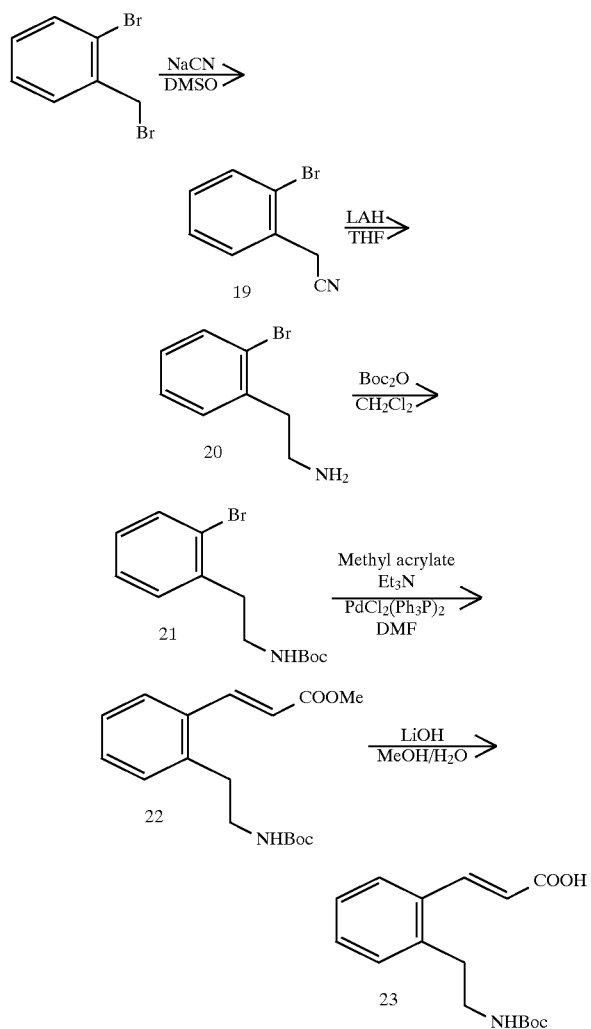

Scheme XIII

N-Boc-protected 4-amino-2-butenoic acid (Compound 27) was prepared via the sequence outlined in the following scheme:

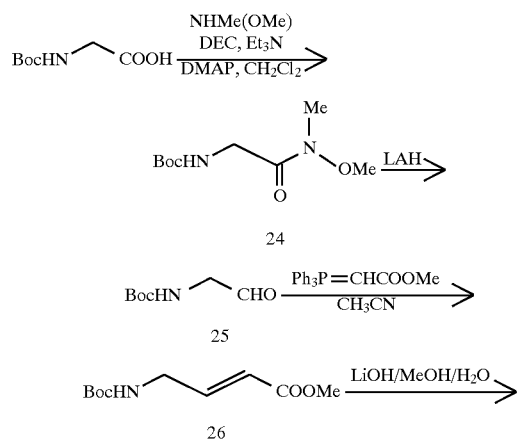

-continued
Scheme XIII

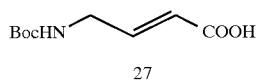

Scheme XIV

N-Boc-protected 6 amino-4,5-(1,2-cyclohexyl)-2-hexanoic acid (Compound 31) and its isomer (Compound 32) were prepared via the sequence outlined in the following scheme:

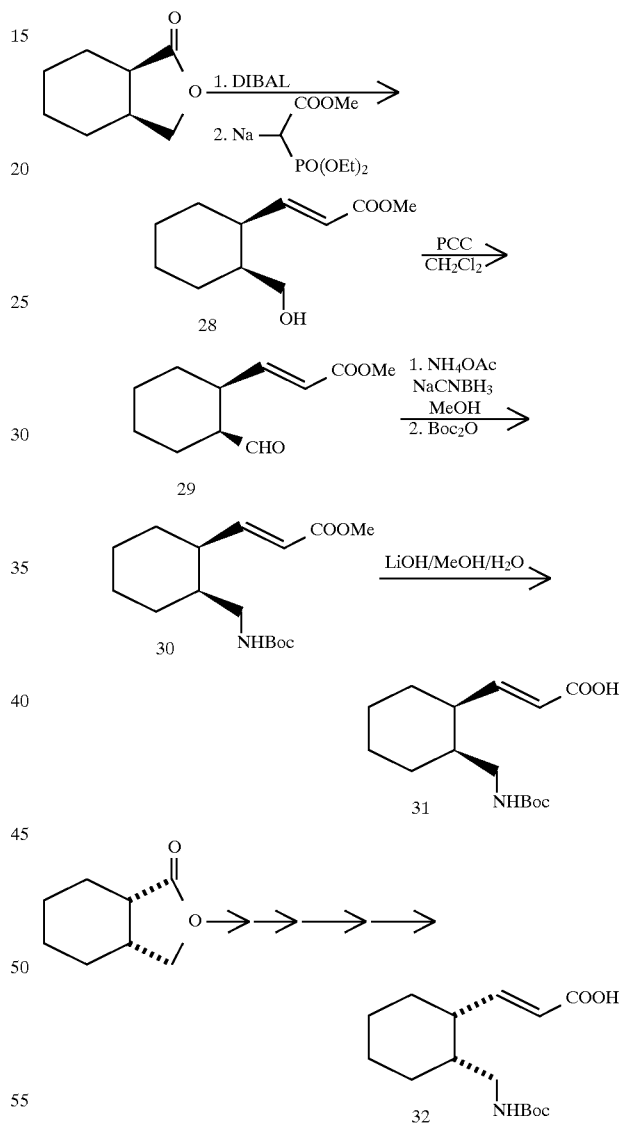

C. Preferred Z and Z' Moieties

Z is an arrangement of atoms which inherently adopt a beta turn conformation and has a positive charge near the distal end. Z can be a group of naturally-occurring or non-naturally-occurring amino acids or it can be an non-amino acid organic moiety. When Z is an amino acid-containing moiety it preferably has the formula E-F-G-H-Cn, wherein E is a direct bond or selected from the group consisting of Ser, Thr, Gly, N-BnGly, Val, Ala, Cys and Tyr;

F is selected from the group consisting of a D-aromatic amino acid and a D-Hype;

G is selected from the group consisting of Oic, Aoc, Thz, octahydro-1H-isoindole-1-carboxylic acid, pipecolinic acid, Pro, 4Hyp, azetidine-2-carboxylic acid, Aib, Leu, Ile, Val, an aromatic amino acid that is Phe, Thi, Tic, indoline-2-carboxylic acid, homoPhe, Trp, Tyr, Nal, and Hype;

H is selected from the group consisting of Arg, Orn, Asn, Gln, and Lys;

Cn is a hydroxyl group or a C-terminal extension selected from the group consisting of carboxamido, alkoxy, an acidic, basic or natural aliphatic, aromatic, or cyclic amino acid residue of the D- or L-configuration.

Most preferably

E is a direct bond or is selected from the group consisting of Ser, Gly and Val;

F is selected from the group consisting of D-Phe, D-Tic and a D-Hype;

G is selected from the group consisting of Phe, Oic, Aoc, Tic and a Hype;

H is Arg; and

Cn is selected from the group consisting of hydroxyl group, an amide group and an alkoxy group.

Preferred Z' moieties correspond to the preferred Z moieties with the exception that they lack the positively charged group, usually a nitrogen-containing moiety, at the distal end. When Z' is an amino acid-containing moiety, it preferably has the formula E-F-G-Cn, wherein E, F and G and Cn are as described above.

A number of non-amino acid-containing beta turn mimetics are known. These molecules may be utilized in place of -F-G- for incorporation of the group into the compounds of this invention. In order to facilitate its incorporation into the bradykinin antagonist compound of this invention by techniques described herein, the beta turn mimetic should have an amino terminus and a carboxyl terminus. Some of such beta turn mimics are illustrated by, but are not limited to, compounds that have been described previously. These include moieties with a phenoxathiin ring system, e.g. 1 (M. Feigel, *J Am. Chem. Soc.* (1986) 108:181–182), bicyclic dipeptides, e.g. (3S, 6S, 9R)-2-oxo-3-amino-7-thia-1-azabicyclo [4.3.0]nonane-9-carboxylic acid 2 (K. Sato and U. Nagui, *J. Chem. Soc.* Perkin Trans. (1986) 1231–1234) and some of its derivatives (U. Nagui and K Sato. *Tet. Lettr* (1985) 26:647–650; U. Nagui and K. Sato: In Deber, C. M.; Hruby, V. J. and Kopple, K. D. (Eds.) *Peptides: Structure and Function, Proceedings of the 9th American Peptide Sympositon*, Pierce Chemical Co., Rockford, Ill., 1985, p. 465), 9-(e.g. 3, G. L. Olson et al. *J. Am. Chem. Soc.* (1990) 112:323–333), 10-(e.g. 4, D. S. Kemp and W. E. Stites, *Tet Lettr* (1988) 40:5057–5060) and Soc. (1988) 110:1638–1639) membered moderately constrained rings, a piperdine ring, e.g. 3-amino-2-piperdine-6-carboxylic acid 6 (D. S. Kemp and P. E. McNamara, *J. Org. Chem.* (1984) 49:2286–2288; D. S. Kemp and P. E. McNamara, *J. Org. Chem.* (1985) 50:5834–5838; D. S. Kemp and E. T. Sun, *Tet Lettr.* (1982) 23:3759–3760; D. S. Kemp and P. McNamara *Tet. Lettr.* (1982) 23:3761–3764), a spirocyclic ring system, e.g. 1,δ-diaza-7-oxospiro[5.4]decane-δ-acetic acid 7 (M. J. Cenin, et al., *J. Org. Chem.* (1993) 51:860–866) and related compounds (M. G. Hinds, et al., *J. Med. Chem.* (1991) 34:1777–1789), and 5H-6-oxo-2,3,4,4a,7,7a-hexahydropyrano[2,3-b]pyrroles, e.g. 8 (J. L. Krstenansky, et al., *Biochem. Biophys. Res. Commun.* (1982) 109:1368–1374; J. L. Krstenansky et al., *J. Heterocyclic Chem.* (1992) 29:707–711).

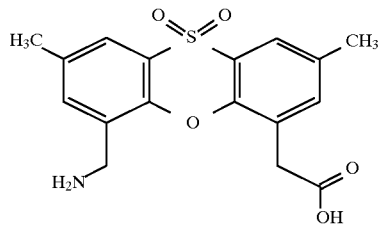

1

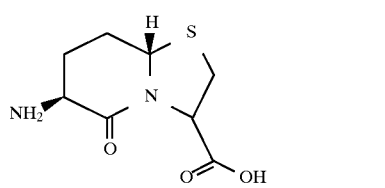

2

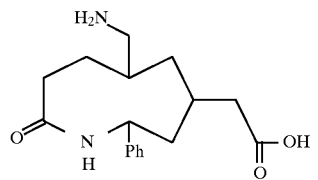

3

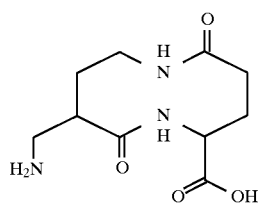

4

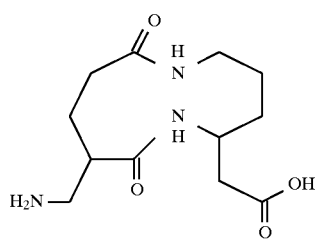

5

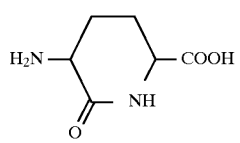

6

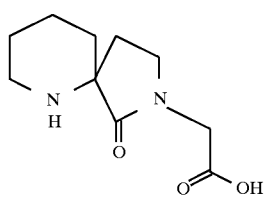

7

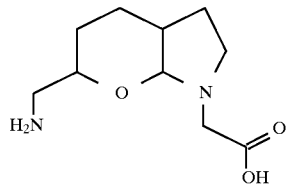

8

In addition to the known beta turn mimetics referred to above, applicants have discovered that certain of the organic moieties described above as being useful Y moieties can also be incorporated into the Z or Z' group, wherein they will act as beta turn mimetics. In particular, the following moieties can be incorporated as beta turn mimetics in the groups Z and Z'.

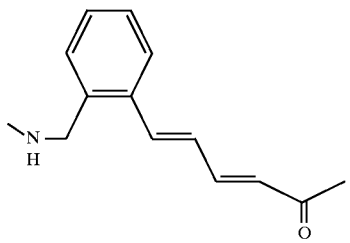
(I)

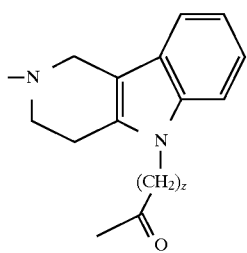
(II)

wherein z is an integer from 1 to 3.

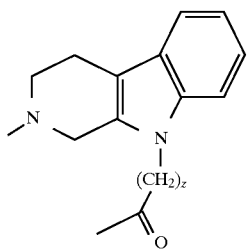
(III)

wherein z is an integer from 1 to 3.

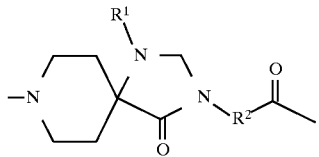
(IV)

wherein $R^1$ is selected from the group consisting of a substituted or unsubstituted aryl group, a straight, branched, saturated or unsaturated lower alkyl chain of 1 to 6 carbon atoms, and a cycloalkyl or cycloalkylmethyl in which the cycloalkyl ring comprises 3 to 6 carbon atoms; and $R^2$ is a saturated or unsaturated alkylene bridge consisting of 1 to 8 carbon atoms optionally substituted with a benzyl or naphthyl group or in which one of the carbon atoms of the bridge is disubstituted to form a cycloalkyl ring consist of 3 to 6 carbon atoms.

The novel beta turn mimetic moieties represented above (I–IV) are incorporated into the bradykinin antagonist compound by the solid phase synthesis procedures described hereinafter, using the corresponding amino-protected acids as intermediates. The appropriate amino-protected acid corresponding to Formula I, i.e. 5-[2-(tert-butoxycarbonylaminomethyl phenyl]-2,4-pentadienoic acid, can be prepared by the procedure described in Example 8. The amino-protected acids corresponding to Formula II can be prepared by procedures described and exemplified in Scheme II and Example 2. The amino-protected acids corresponding to Formula III can be prepared by procedures described and exemplified in Example 3. Amino-protected acids corresponding to Formula IV can be prepared by the procedure outlined in Scheme VI.

When a non-amino acid containing beta turn mimetic moiety is incorporated into Z or Z', it may be linked at its amino-terminus to the Y moiety either by a direct bond or through an amino acid residue, including any of the amino acids included in the definition of E. When the non-amino acid containing beta turn mimetic moiety is incorporated into the group Z—that is, when one desires to prepare a $B_2$ receptor antagonist—it is bonded at its terminal carbonyl carbon to a positively charged group. When the non-amino acid containing beta turn mimetic moiety is incorporated into the group Z'—that is, when one desires to prepare a $B_1$ receptor antagonist—it is bonded at its terminal carbonyl carbon to the group Cn, wherein Cn has the previously described meaning.

The positively charged group which is bonded to the non-amino acid containing beta turn mimetic in Z can be an amino acid containing group of the formula -H-Cn, wherein H and Cn have the previously described meanings. Preferably, H is Arg and Cn is selected from the group consisting of hydroxyl, an amide group and an alkoxy group.

Alternatively, the positively charged group can be a non-naturally occurring amino acid group (which can be in the D- or L-configuration) which acts as an arginine mimetic. Exemplary of arginine mimetics are

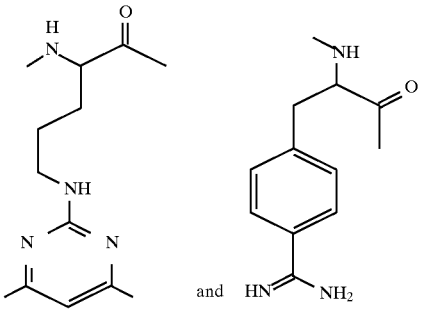

The amino acids corresponding to these two arginine mimetic moieties can be prepared, respectively, by the procedures described in *Biochemistry* (1975) 14(23) :5194–5195 and *Pharmazie* (1974) 29(l):12–15.

Thus, when a non-amino acid containing beta turn mimetic moiety is employed, the group Z can be defined as -E-β-H'-Cn and the group Z' can be defined as -E-β-Cn, wherein E and Cn have the previously defined meanings, β represents the non-amino acid containing beta turn mimetic and H' represents Arg, Orn, Asn, Gln, Lys or an arginine mimetic. In such compounds, E is preferably selected from the group consisting of a direct bond, Ser, Gly and Val; H' is preferably selected from Arg, and Cn is preferably selected from the group consisting of hydroxyl, amide or alkoxy.

The following terms used herein in the specification and claims are further defined:

"olefinic aminoalkenoyl" is a carbon chain of from 2 to 18 carbons containing at least one double bond, wherein 2 to 4 carbons may be optionally incorporated into a cyclic structure, having an amino acid linkage (i.e., an N-terminal amino group and a C-terminal carbonyl group). The alkenyl portion of the olefinic aminoalkenoyl is preferrably a hydrocarbon chain, but may also include carbon replacements, such as by nitrogen.

"Hype" is defined herein as having the following structure:

wherein R is selected from the group consisting of H, $C_1$–$C_6$ alkyl, substituted $C_1$–$C_6$ alkyl, $C_2$–$C_8$ alkenyl, $C_2$–$C_8$ cycloalkyl, $C_3$–$C_8$ cycloalkyl substituted $C_1$–$C_6$ alkyl, an aryl group, a substituted aryl group wherein the substituent is $C_1$–$C_4$ alkyl, $C_1$–$C_4$ alkoxy, halogen or trifluoromethyl, an arylalkyl group, and a group of the formula $R^1$NHC(O) where $R^1$ is $C_1$–$C_6$ alkyl or aryl, and where X is either $SO_n$ or oxygen, and n=0, 1, or 2;

"carbocycle" and "cycloalkyl" are interchangeably defined herein as a saturated cyclic hydrocarbon structure, such as cyclohexyl, cyclopropyl, cyclobutyl, cyclopentyl and cycloheptyl, this definition includes mono- and polycyclic structures;

"olefin" and "cycloalkenyl" are defined herein as a cyclic hydrocarbon structure containing at least one double bond and includes substituted aryl groups, such as 1,2-, 1,3- and 1,4-phenylene,benzyl, phenyl, cyclohexenyl, cyclohexadienyl, cyclopentadienyl. Also included in this definition are multiple ring structures, such as naphthyl;

"pseudopeptide" is an entity which is partially amino acid (peptidic) in nature and partially organic chemical in nature. A minimum of two peptide bonds are eliminated and replaced by organic molecules having the ability to retain the functionality of amino acids they replace in the pseudopeptides of the present invention;

"alkenyl" and "olefin" are interchangeably defined herein as a hydrocarbon structure containing at least one double bond, suitable alkenyls can also be hydrocarbon structure containing multiple double bonds, the double bonds can optionally be incorporated into a ring structure, such as a cycloalkenyl;

"amino acid linkage" is exemplified by a moiety having a N-terminal amino group and a C-terminal carbonyl group;

"alkyl" is a paraffinic hydrocarbon group which may be derived from an alkane by dropping one hydrogen from the formula, such as methyl, ethyl, propyl, isopropyl, butyl, and so forth;

"substituted $C_1$–$C_6$ alkyl" is a branched alkyl, such as methylbutyl;

"aryl" is an aromatic ring compound such as phenyl, naphthyl;

"substituted aryl" is a substituted aromatic ring including, but not limited to, nitro substitution, or halogen substitution; and "aralkyl" is a aryl being attached through an alkyl chain, straight or branched, containing from one through six carbons, such as a phenylpropyl group.

A "direct bond" is a bond which replaces a particular amino acid compound between adjacent amino acids and which amino acid may also be indicated to be absent by the term "null".

The phrase "a suitable amine protecting group" is a group, such as Boc (t-butyloxycarbonyl-) which protects the amine moiety from reaction and which can be removed under mild conditions so as not to affect the rest of the molecule.

Definitions of the amino acid abbreviations used herein are as follows:

"amino acid" is the basic structural unit of proteins, consisting of an amino group, a carboxyl group, a hydrogen atom and a distinctive R group (side chain) bonded to a carbon atom. There are 20 naturally occurring amino acids which have the following abbreviations: Ala is alanine; Arg is arginine; Asn is asparagine; Asp is aspartic acid; Cys is cysteine; Gin is glutamine; Glu is glutamic acid; Gly is glycine; His is histidine; Ile is isoleucine; Leu is leucine; Lys is lysine; Met is methionine; Phe is phenylalanine; Pro is proline; Ser is serine; Thr is threonine; Trp is tryptophan; Tyr is tyrosine; and Val is valine. There are also numerous well-known non-naturally occurring amino acids which include, but are not limited to the following: Aib is 2-aminoisobytyric acid; Aoc is (S,S,S)-2-azabicyclo[3.3.0] octane-3-carboxylic acid; Eac is e-aminocaproic acid; Nal is beta-2-naphthylalanine; Orn is ornithine; dehydroPro is 3,4-dehydroproline, homoPhe is homophenylalanine; 4Hyp is 4-hydroxyproline; Sar is sarcosine; Thi is beta-2-thienylalanine; Thz is thiazolidine-4-carboxylic acid; phenylGly is 2-phenylglycine; Tic is tetrahydroisoquinoline-3-carboxylic acid; Oic is (2S, 3aS, 7aS)-octahydro-1H-indole-2-carboxylic acid; phenyl is a 3-methyl-2-butenyl radical. "aromatic amino acid" is a naturally occurring or non-naturally occurring amino acid having one or more unsaturated carbon rings and includes, but is not limited to, Phe, Tic, Thi, n-benzyl Gly, homoPhe, Tyr, Trp, indoline-s-carboxylic acid, Nal.

D-Hype (trans-propyl) is 4S-D-prolyl propyl ether and represents:

D-Hype (trans-thiophenyl) is 4S- D-prolyl phenyl thioether, also known as D-4-hydroxyproline trans phenylthioether also known as D-Hyp S(trans-phenyl) and represents:

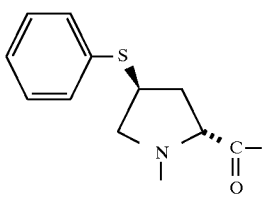

D-Hype (trans-phenylpropyl) represents:

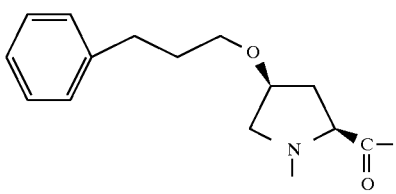

D-Hype (trans-2-methylbutyl) represents:

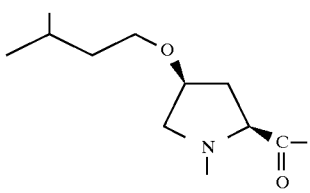

D-Hype (trans-ethyl) represents:

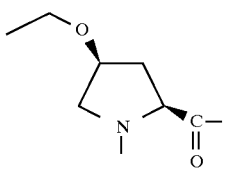

D-Hype (trans-methyl) represents:

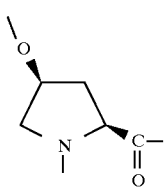

Aoc can be prepared by the method of V. Teetz, R. Geiger and H. Gaul, *Tetrahedron Lett.* (1984):4479. Tic is commercially available from Bachem Biosciences or can be prepared by the method of K. Hayashi, Y. Ozaki, K. Nunami and N. Yoneda, *Chem. Pharm. Bull.* (1983) 31:312.

All amino acids residues, except Gly and Ser, described in the specification are preferably of the L-configuration unless otherwise specified. It would be recognized, however, that the 7 position amino acids and derivatives must always be the D-configuration whereas the amino acids and derivatives of position 8 may be either in the D- or L-configuration. The hydroxyproline ethers at position 7 are preferably in a trans configuration, whereas the hydroxyproline ethers at position 8 can be in either the cis or trans configuration. The symbols and abbreviations used for amino acids, their derivatives and protecting groups, and peptides and their salts are those customarily used in peptide chemistry. (See *Biochem. J.* (1972) 126:773), which Journal reference is hereby incorporated by reference.

The synthesis of the peptides of this invention including derivation, activation, and coupling of protected amino acid residues, and their purification, and the analytical methods for determining identity and purity are included in the general body of knowledge of peptide chemistry, as described in *Houben Weyl Methoden der Organischen Chemie* (1974) Vol.16, parts I & II for solution-phase synthesis, and in *Solid Phase Peltide Synthesis*, (1984), by Stewart and Young for synthesis by the solid-phase method of Merrifield.

Any chemist skilled in the art of peptide synthesis can synthesize the peptides of this invention by standard solution methods or by manual or automated solid phase methods.

The appropriate hydroxyproline substituents used at position 7 or 8 are prepared by the process described in PCT publications WO 92/18155 and WO 92/18156 which are herein incorporated by reference. The starting materials are commercially available and can be prepared by known procedures. Both the cis and trans stereoisomers can be prepared by these means and are within the scope of the present invention.

ADMINISTRATION AND USE

Therapeutic applications of the novel bradykinin antagonists include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic inflammatory or pathological conditions which are known to be mediated by bradykinin or exacerbated by an overproduction of bradykinin can also be achieved. These conditions include inflammatory disorders such a s shock, systemic inflammatory response syndrome, pancreatitits, and angioedema, arthritis and inflammatory bowel disease, systemic treatment of pain and inflammation, local trauma such as wounds, burns, rashes, airway disorders such as asthma, rhinitis and allergies, and nervous system diseases such as spinal cord injury, stroke, hemorrhage, trauma, tumors, abcess and encephalitis. The compounds of the invention which are $B_1$ receptor antagonists are useful, alone or in combination with the $B_2$ receptor antagonists, for the treatment of conditions associated with persistent inflammatory hyperalgesia, e.g. rheumatoid arthritis.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules, or tablets which may contain diluents, dispersing and surface active agents, binders and lubricants which materials are all well known to the ordinary skilled artisan.

In the case of oral administration, fine powders or granules of the compound may be formulated with diluents and dispersing and surface active agents, and may be prepared in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening, and emulsifying agents. The granules or tablets for oral administration may be coated or other pharmaceutically acceptable agents and formulations may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs are suitably prepared using known polymeric materials such as various acrylic-based polymers selected to provide desired release characteristics. Suppositories are prepared from standard bases such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 500 mg/kg of active compound, preferably 0.1 to 50 mg/kg. Persons skilled in the art using routine clinical testing are able to determine optimum doses for the particular ailment being treated. The desired dose is administered to a subject from 1 to 6 or more times daily, intravenously, orally, rectally, parenterally, topically, or by inhalation.

The efficacy of the inventive compounds of this invention as bradykinin receptor antagonists can be determined using the bradykinin binding and tissue assays described herein. The results of these assays demonstrate that the novel compounds are potent, selective bradykinin receptor antagonists.

The following examples are illustrative of preferred embodiments of methods of preparation and compounds of the invention and are not to be construed as limiting the invention thereto.

The preparation of various specific hydrophobic spacer groups (Y) useful for incorporation into the bradykinin antagonists at the invention are exemplified in the following Examples 1 through 7.

EXAMPLE 1

1,2-Benzo-8-tert-butoxycarbonyl-4-keto-3, 8-diazaspiro[4.5]decan-3-acetic Acid

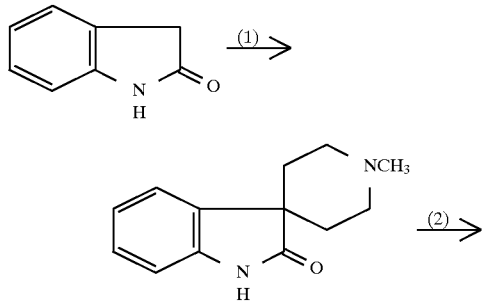

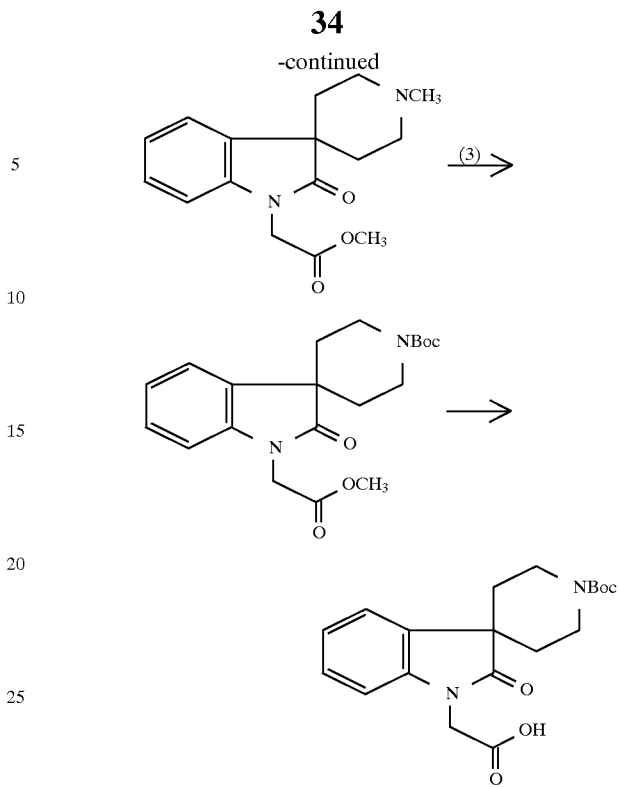

(1) Preparation of 1,2-benzo-4-keto-8-methyl-3,8-diazaspiro[4.5]decane.

A stirred solution of 6.65 g (50 mmol) of oxindole in 100 ml of tetrahydrofuran was cooled to −78° C. and 250 ml (250 mmol) of a 1M solution of sodium bis(trimethylsilyl)amide in tetrahydrofuran was added dropwise. The mixture was stirred for 30 minutes at −78° C. and then 9.63 g (50 mmol) of N-methyl bis(2-chloroethyl)amine hydrochloride was added. After the mixture was stirred at −78° C. for 30 minutes, it was allowed to come to ambient temperature and stirring was continued for 18 hours. Water (100 ml) was added and the mixture was extracted three times with ether. The ether extracts were washed with brine, dried ($Na_2SO_4$) and concentrated. The residue was chromatographed (silica gel, eluting with a 5 to 50% gradient of methanol in methylene chloride) to give 7.17 g (66%) of the product as tan crystals, mp 200°–205° C. (dec).

(2) Preparation of methyl 1,2-benzo-8-methyl-4-keto-3,8-diazaspiro[4.5]decan-3-acetate.

To a stirred suspension of sodium hydride (1.60 g, 40 mmol, 60% dispersion in mineral oil) in 10 ml of dimethylformamide a solution of 7.07 g (32.7 mmol) of 1,2-benzo-4-keto-8-methyl-3, 8-diazaspiro[4.5]decane in 50 ml of dimethylformamide was added dropwise. After the mixture was stirred at 0° C. for 30 minutes, 3.8 ml of methyl bromoacetate was added and then the mixture was stirred at ambient temperature for 5 hours.

The mixture was poured into 500 ml of water and extracted with five portions of ether. The ether extracts were washed with water, then brine, dried ($Na_2SO_4$), and concentrated. The residue was chromatographed on a silica gel column, eluting with a 1 to 25% gradient of methanol in methylene chloride to give 7.93 g. (84%) of the product as crystals, mp 100°–103° C.

(3) Preparation of methyl 1,2-benzo-8-tert-butoxycarbonyl-4-keto-3,8-diazaspiro[4.5]decan-3-acetate.

A mixture of 3.26 g (11.3 mmol) of methyl 1,2-benzo-8-methyl-4-keto-3, 8-diazaspiro[4.5]decan-3-acetate, 7.5 ml (45.1 mmol) of 2,2,2-trichloroethyl chloroformate and 100 ml of toluene was stirred and refluxed for 18 hours. After being cooled to ambient temperature, the mixture was diluted with 200 ml of ether, washed with water, dried (NaSO$_4$) and concentrated. The residual oil was dissolved in 30 ml of acetic acid and 10 g of zinc dust was added. After the initial exotherm subsided the reaction mixture was stirred for 1 hour, 50 ml of methylene chloride was added and the mixture was filtered through diatomaceous earth. The filtrate was diluted with 50 ml of water, cooled to 0° C. and made alkaline with concentrated aqueous ammonia. The layers were separated and aqueous phase was extracted with methylene chloride. The combined organic solutions were washed with brine, dried (Na$_2$SO$_4$) and concentrated. The residue was dissolved in 50 ml of dioxane. The solution was cooled to 0° C. and a solution of di-tert-butyl dicarbonate in 10 ml of dioxane was added. After being stirred at 25° C. for 16 hours, the reaction mixture was diluted with 100 ml of ether and 25 ml of water. The layers were separated and the aqueous phase was extracted three times with ether. The combined organic extracts were washed with water and brine, dried (Na$_2$SO$_4$) and concentrated. The residue was chromatographed on a silica gel column eluting with a 0 to 5% gradient of methanol in methylene chloride to give 3.82 g (90.3%) of the product as colorless crystals, mp 135°–136° C.

(4) Preparation of 1,2-benzo-8-tert-butoxycarbonyl-4-keto-3,8-diazaspiro[4.5]decan-3-acetic acid.

A stirred mixture of 3.76 g (10 mmol) of methyl 1,2-benzo-8-tert-butoxycarbonyl-4-keto-3, δ-diazaspiro[4.5]decan-3-acetate, 4.24 g (40 mmol) of sodium carbonate, 50 ml of methanol and 50 ml of water was heated at reflux for 2 hours. Methanol solvent was distilled off and the resulting solution was diluted with water, cooled to 0° C. and acidified with 5N hydrochloric acid. The mixture was extracted five times with ethyl acetate. The extracts were washed with brine, dried (Na$_2$SO$_4$) and concentrated. Recrystallization of the residue from ethanol afforded 2.67 g (74.2%) of the product as crystals, mp 225°–228° C. (dec).

EXAMPLE 2

5-[2-(tert-Butoxycarbonyl)-1,2,3,4-tetrahydro-5H-pyrido[4,3-b]indole]acetic Acid

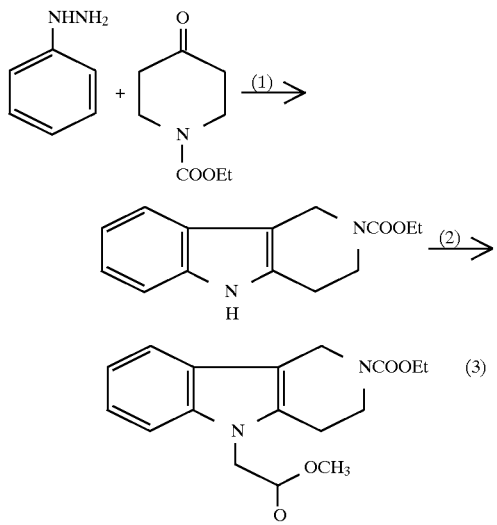

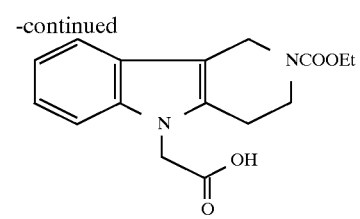

(1) Preparation of 2-carbethoxy -1,2,3,4-tetrahydro-5H-pyrido[4,3-b] indole.

A stirred mixture of 5.2 g (30 mmol) of 1-carbethoxy-4-piperidone and 4.34 g (30 mmol) of phenylhydrazine hydrochloride in 9 ml of pyridine under argon was heated in an oil bath at 110°–115° C. for 18 hours. After being cooled to 25° C., the reaction mixture was diluted with water and extracted with ethyl acetate. The extract was washed with water, dried over Na$_4$SO$_4$ and concentrated. Chromatography of the residue on a silica gel column eluting with a 0 to 30% gradient of ethyl acetate in hexane afforded the product (80%) as colorless crystals, mp 126°–127° C.

(2) Preparation of methyl 5-[2-carbethoxy-1,2,3,4-tetrahydro-5H-pyrido[4,3-b]indole]acetate.

To a stirred suspension of 264 mg (11 mmol) of sodium hydride in 15 ml of dimethylformamide under argon at 5° C. was added dropwise a solution of 2.44 g (10 mmol) of 2-carbethoxy-1,2,3,4-tetrahydro-5H-pyrido 4,3-b]indole in 15 ml of dimethylformamide. After the mixture was stirred at 25° C. for 30 minutes, 1.53 g (10 mmol) of methyl bromoacetate was added and stirring at 25° C. was continued for 24 hours. The reaction mixture was quenched by addition of a 100 ml of a saturated aqueous ammonium chloride solution. The mixture was extracted with ethyl acetate. The extract was washed with water, dried (Na$_2$SO$_4$) and concentrated. Chromatography of the residue on silica gel eluting with a 0 to 30% gradient of ethyl acetate in hexane gave the product (67%) as an oil.

(3) Preparation of 5-[2-(tert-butoxycarbonyl)-1,2,3,4-tetrahydro-5H-pyrido[4,3-b]indole]acetic acid.

After a mixture of 1.63 g (mmol) of methyl 5-[2-carbethoxy-1,2,3,4-tetrahydro-5H-pyrido[4,3-b]indole] acetate, 5.2 ml of 10% aqueous potassium hydroxide solution and 20 ml of ethanol was stirred and refluxed for 20 hours, it was cooled to 25° C., the pH was adjusted to 9 by addition of 1N hydrochloric acid, 1.5 g (6.9 mmol) of di-tert-butyl dicarbonate was added and stirring was continued for an additional 18 hours. The mixture was concentrated to remove ethanol and then it was extracted with ethyl acetate. The extract was dried (Na$_2$SO$_4$) and concentrated. Recrystallization of the residual solid from ethyl acetate gave 1.1 g (64%) of the product as a crystalline solid, mp 202°–203° C.

EXAMPLE 3

3-[9-[2-(tert- Butoxycarbonyl)-1,2,3,4-tetrahydro-9H-pyrido[3,4-b]indole]-propanoic Acid

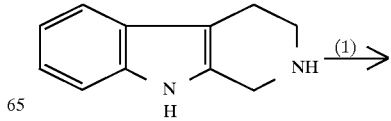

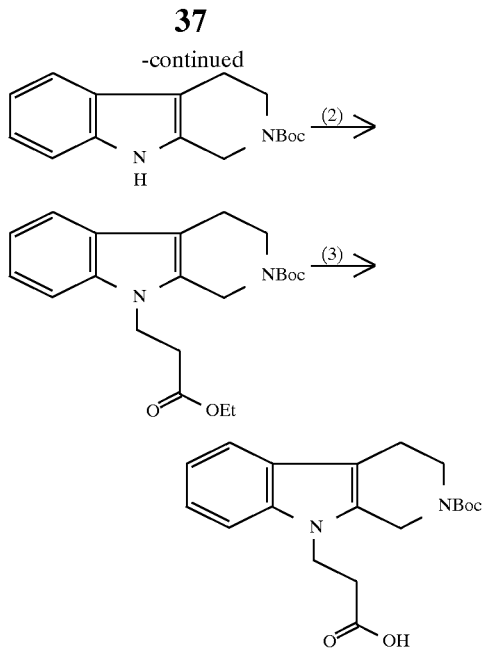

(1) Preparation of 2-(tert-butoxycarbonyl)-1,2,3,4-tetrahydro-9H-pyrido[3,4-b]indole.

Di-tert-butyl dicarbonate (14.5 ml, 61.2 mmol) was added to a stirred mixture of 10.1 g (57.5 mmol) of 1,2,3,4-tetrahydro-9H-pyrido[3,4-b] indole and 6.17 g (58.1 mmol) of sodium carbonate in 120 ml of water and 100 ml of 2-propanol at 25° C. After being stirred at 25° C. for 16 hours the mixture was diluted with 100 ml of water and extracted with ethyl acetate. The extracts were washed with brine, dried over sodium sulfate and concentrated. The residual solid was recrystallized from ethyl acetate-hexane to afford 15.36 g (98%) of product as colorless crystals, mp 150°–151° C.

(2) Preparation of ethyl 3-[9-[2-(tert-butoxycarbonyl-1,2,3,4-tetrahydro-9H-pyrido[3,4-b]indole]]propanoate.

To a stirred suspension of 0.4 g (13.3 mmol) of an 80% dispersion of sodium hydride in mineral oil in 50 ml of dimethylformamide at 25° C. under argon was added in portions 3.0 g (11.0 mmol) of 2-(tert-butoxycarbonyl)-1,2,3,4-tetrahydro-9H-pyrido[3,4-b]indole. After the mixture was stirred at 25° C. for 30 minutes, 1.6 ml (12.5 mmol) of ethyl 3-bromopropanoate was added. The resulting mixture was stirred at ambient temperature for 16 hours and then it was acidified to Congo red with 5N hydrochloric acid. The mixture was extracted with ethyl acetate. The extracts were washed with brine, dried over sodium sulfate and concentrated to afford the crude product as an oil.

(3) Preparation of 3-[9-[2-tert-butoxycarbonyl)-1,2,3,4-tetrahydro-9H-pyrido[3,4-b]indole]]-propanoic acid.

Crude ethyl 3-[9-[2-(tert-butoxycarbonyl)-1,2,3,4-tetrahydro-9H-pyrido [3,4-b]]indole]propanoate, prepared as described above, was dissolved in 20 ml of methanol. Sodium hydroxide (3N, 7.5 ml, 2.25 mmol) was added to the methanoic solution and the mixture was stirred at ambient temperature for 16 hours. After the reaction mixture was diluted with water, it was extracted with ether. The aqueous phase was brought to pH 4 with 5N hydrochloric acid. The mixture was extracted with ethyl acetate. The extracts were dried over sodium sulfate and concentrated. Residual solid was recrystallized from methanol-ethyl acetate to afford 2.81 g (74%) of the product as fine crystals, mp 152°–153.5° C.

9-[2-(tert- Butoxycarbonyl)-1,2,3,4-tetrahydro-9H-pyrido [3,4-b[indole] acetic acid was prepared by the method of this example employing ethyl bromoacetate in place of ethyl 3-bromopropanoate to give colorless crystals, mp 80° C. (dec).

EXAMPLE 4

7-(9-Fluorenylmethoxycarbonylamino)-4-methyl-2-quinolinon-1-acetic Acid

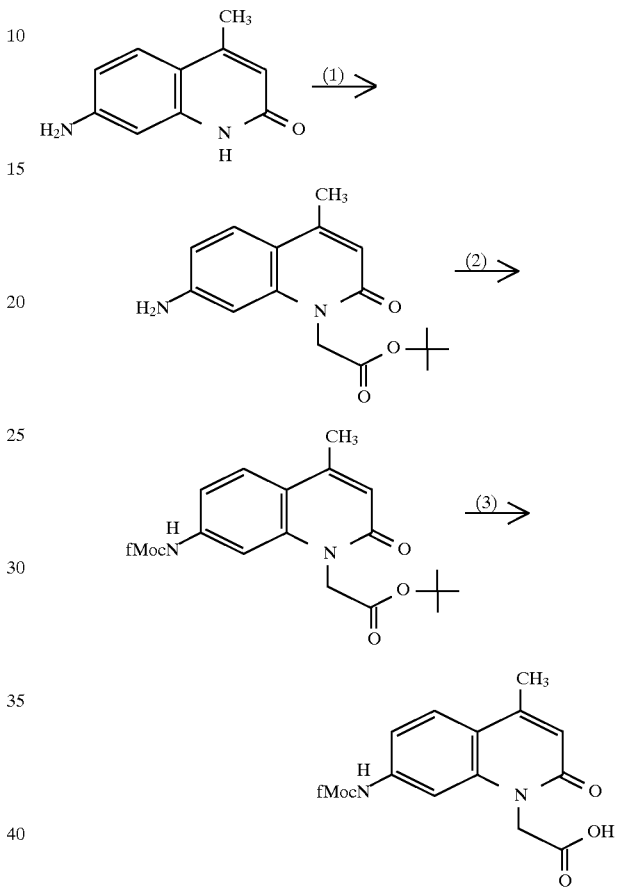

(1) Preparation of tert-butyl 7-amino-4-methyl-2-quinolinon-1-acetate.

Sodium hydride (450 mg of an 80% dispersion in mineral oil, 15 mmol) was added to a stirred solution of 2.5 g (14.3 mmol) of 7-amino-4-methyl-2-quinolone [*J. Org. Chem.* (1991) 56:980–983] in 40 ml of dimethylformamide under argon at 0° C. After the mixture was stirred for 30 minutes at 25° C., 3 g (15.4 mmol) of tert-butyl bromoacetate was added and stirring was continued for 24 hours. The mixture was poured into 200 ml of water and extracted three times with methylene chloride. The extracts were washed with water, dried (Na$_2$SO$_4$) and concentrated. Recrystallization of the solid residue from ethyl acetate afforded 2.6 g (70%) of the product as crystals, mp 191°–193° C.

(2) Preparation of tert-butyl 7-(9-fluorenylmethoxycarbonylamino)-4-methyl-2-quinolon-1-acetate.

9-Fluorenylmethoxycarbonyl chloride (2 g, 7.74 mmol) was added to a stirred solution of 2 g (6.94 mmol) of tert-butyl-7-amino-4-methyl-2-quinolon-1-acetate in 60 ml of dioxane. After addition of a solution of 0.84 g of sodium bicarbonate in 10 ml of water, the mixture was stirred at 25° C. for 3 hours. An additional 0.5 g of 9-fluorenylmethoxycarbonyl chloride was then added and stirring at 25° C. was continued for a further 20 hours. The residue was suspended in methylene chloride and filtered. The filtrate was concentrated and the residual solid was recrystallized from methylene chloride-ethyl acetate to give 1.75 g (32.8%) of the product as crystals, mp 223°–224° C.

(3) Preparation of 7-(9-fluorenylmethoxycarbonylamino)-4-methyl-2-quinolinon-1-acetic acid.

A solution of 2 g (3.92 mmol) of tert-butyl 7-(9-fluorenylmethoxy-carbonylamino)-4-methyl-2-quinolon-1-acetate in 60 ml of a 1:1 mixture of trifluoroacetic acid and methylene chloride was stirred at 25° C. for 24 hours. The solvents were removed in vacuo and the residue was recrystallized from chloroform-tetrahydrofuran to yield 75 g (93.5%) of the product as colorless crystals, mp 256°–257° C.

EXAMPLE 5

5-(3-tert-Butoxycarbonylamino-6(5H) phenanthridinone)acetic Acid

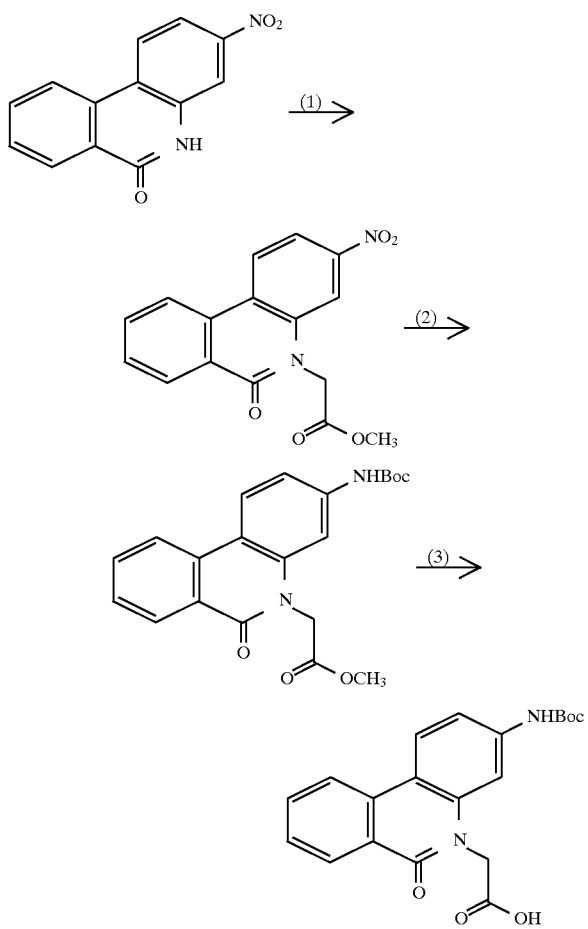

(1) Preparation of methyl 5-(3-nitro-6(5H) phenanthridinone)acetate Acetate.

To a stirred mixture of 0.3 g (10 mmol) of an 80% dispersion of sodium hydride in mineral oil in 40 ml of dimethylformamide under argon at 0° C. was added in portions 2.0 g (8.3 mmol) of 3-nitro-6(5H)phenanthridinone (Rare Chemical Collection, Aldrich Chemical Co., Milwaukee, Wis.). The mixture was stirred for 30 minutes and then 0.95 ml (10 mmol) of methyl bromoacetate was added and stirring was continued for 20 hours at 25° C. The precipitated product was filtered, washed with water and dried over phosphorus pentoxide in a vacuum desiccator. The solid product was used for further reaction without additional purification.

(2) Preparation of methyl 5-(3-tert-butoxycarbonylamino-6 (5H)phenanthridinone)acetate.

A mixture of 1.70 g (5.4 mmol) of crude solid methyl 5-(3-nitro-6(5H) phenanthridinone)-acetate, prepared as described above, 100 mg of 10% palladium-on-carbon catalyst and 100 ml of ethanol was hydrogenated on a Parr apparatus for 24 hours at 25° C. and an initial pressure of 60 psi of hydrogen. The mixture was filtered and the filtrate was concentrated in vacuo. After a mixture of the residue, 2.38 g (10 mmol) of di-tert-butyl dicarbonate, 0.87 of sodium carbonate, 20 ml of 2-propanol and 20 ml of water was stirred at 25° C. for 48 hours, it was adjusted to pH 3 with 5N hydrochloric acid and extracted with ethyl acetate. The extract was washed with brine, dried over sodium sulfate and concentrated in vacuo. Column chromatography of the residue (silica gel, ethyl acetate:hexane 1:4) gave 0.45 g (22%) of the product as an oil.

(3) Preparation of 5-(3-tert-butoxycarbonylamino-6(5H) phenanthridinone)acetic acid.

A stirred mixture of 0.88 g (2.3 mmol) of methyl 5-(3-tert-butoxycarbonylamino-6(5H) phenanthridinone)acetate and 1.0 g (9.4 mmol) of sodium carbonate in 25 ml of methanol and 25 ml of water was heated at reflux for 2 hours. The methanolic solvent was distilled off and then the reaction mixture was adjusted to pH3 with 5N hydrochloric acid. The precipitated solid was recrystallized from ethyl acetate-hexane to afford the product as yellow crystals, mp 259°–261° C.

EXAMPLE 6

1-tert-Butoxycarbonyl-4-piperidinyl)-2-benzimidazolone-3-acetic Acid

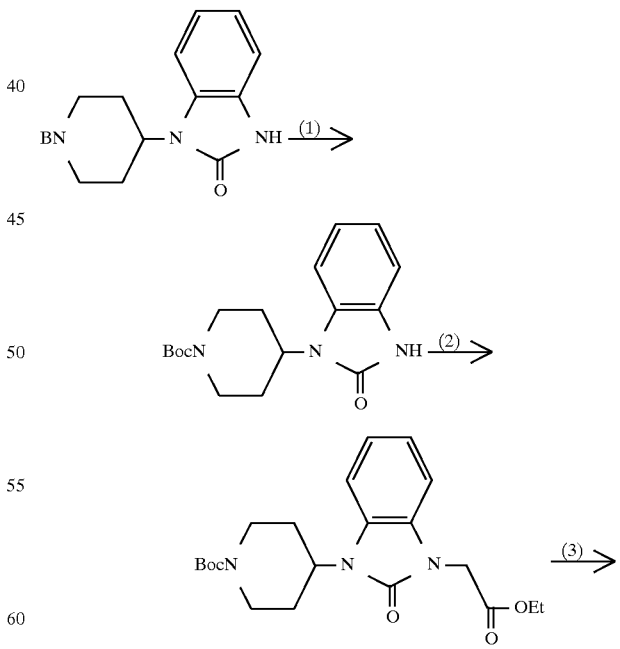

(1) Preparation of 1-(1-tert-Butoxy-4-piperidinyl)-2-benzimidazolone.

A mixture of 5.13 g (23.1 mmol) of 1-(4-piperidinyl)-2-benzimidazolone, 3.71 g (35 mmol) of sodium carbonate, and 5.5 ml (23.9 mmol) of di-tert-butyl dicarbonate in 40 ml of water and 40 ml of 2-propanol was stirred for 16 hours at 25° C. After the mixture was extracted with ethyl acetate, the combined extracts were washed with brine and dried over sodium sulfate. Removal of solvent provided a solid residue that was recrystallized from ethyl acetate to give the product as 6.20 g (92%) of colorless crystals, mp 162°–163° C.

(2) Preparation of ethyl 1-(1-tert-Butoxycarbonyl-4-piperidinyl)-2-benzimidazolone-3-acetate.

To a stirred suspension of 0.76 g (25.3 mmol) of sodium hydride in 85 ml of tetrahydrofuran under argon was added 5.08 g (16.0 mmol) of 1-(1-tert-butoxycarbonyl-4-piperidinyl)-2-benzimidazolone. After the mixture was stirred for 30 minutes at ambient temperature, 2.1 ml (17.4 mmol) of ethyl iodoacetate was added dropwise. The resulting mixture was stirred at reflux temperature for 5 hours and at ambient temperature for 16 hours and then it was concentrated in vacuo. After a solution of the residue in ethyl acetate was washed successively with 0.1N hydrochloric acid, a saturated aqueous solution of sodium bicarbonate and brine, it was dried over sodium sulfate and concentrated. Flash chromatography of the residue (silica gel, ethyl acetate:hexane 1:1) afforded 4.41 g (68%) of the product as an amorphous solid.

(3) Preparation of 1-(1-tert-butoxycarbonyl-4-piperidinyl)-2-benzimidazolone-3-acetic acid.

To a stirred solution of 4.20 g (10.4 mmol) of ethyl 1-(1-tert-butoxycarbonyl-4-piperidinyl)-2-benzimidazolone-3-acetate in 30 ml of methanol was added dropwise 5.8 ml (17.4 mmol) of 3N sodium hydroxide. After the resulting mixture was stirred for 16 hours at 25° C., water was added and it was extracted with ether. The aqueous phase was acidified to Congo red with 5N hydrochloric acid and the mixture was extracted with ethyl acetate. The extracts were dried over sodium sulfate and concentrated. Recrystallization of the residue from ethyl acetate-methanol gave 3.60 g (92%) of the product as colorless crystals, mp 208°–210° C.

EXAMPLE 7

N-Benzoyl-N-(3-tert-butoxycarbonylaminophenyl) glycine

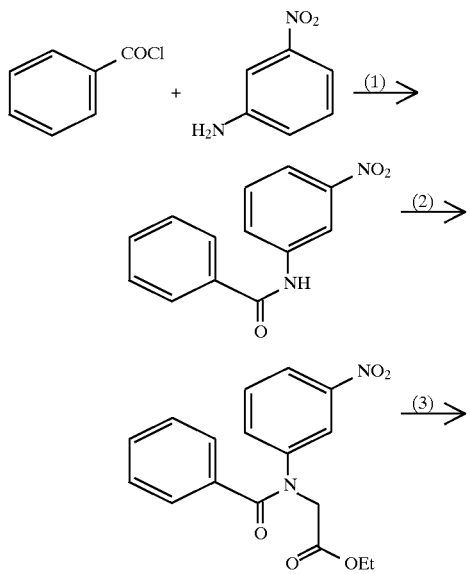

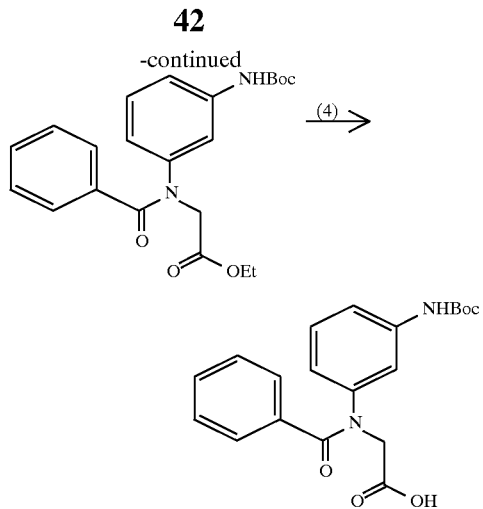

(1) Preparation of N-benzoyl-3-nitroaniline.

To a stirred mixture of 5.0 g (35.5 mmol) of 3-nitroaniline and 6.0 ml (452.6 mmol) of triethylamine in 100 ml of methylene chloride at 25° C. under argon of benzoyl chloride (5.0 ml, 43.1 mmol) was added dropwise. The resulting mixture was stirred at ambient temperature for 16 hours, washed successively with 1N hydrochloric acid, saturated aqueous sodium bicarbonate solution and brine, dried ($Na_2SO_4$) and concentrated. The residue was recrystallized from methylene chloride to give 6.59 g (77%) of the product as fine crystals, mp 154°–155° C.

(2) Preparation of ethyl N-benzoyl-N-(3-nitrophenyl) glycinate.

To a stirred suspension of 0.93 g (31 mmol) of an 80% dispersion of sodium hydride in mineral oil in 75 ml of dimethylformamide at 25° C., under argon, was added in portions 5.0 g (20.6 mmol) of N-benzoyl-3-nitroaniline. After the mixture was stirred at 25° C. for 30 minutes 3.5 ml (31 mmol) of ethyl 2-bromoacetate was added dropwise and stirring was continued for 3 hours. The mixture was quenched with 100 ml of saturated aqueous ammonium chloride solution and extracted 3 times with ethyl acetate. The extracts were washed with brine, dried ($Na_2SO_4$) and concentrated. The residue was chromatographed (silica gel, ethyl acetate:hexane 1:3) to provide 6.35 g (94%) of the product as a light yellow oil.

(3) Preparation of ethyl N-benzoyl-N-(3-benzyloxycarbonyl-aminophenyl)glycinate.

A mixture of 3.01 g (9.0 mmol) of ethyl N-benzoyl-N-(3-nitrophenyl)-glycinate, 3.0 ml (12.7 mmol) of di-tert-butyl dicarbonate, 0.6 g of 10% palladium-on-carbon catalyst and 100 ml of ethanol was hydrogenated on Parr apparatus at 25° C. and an initial hydrogen pressure of 60 psi for 24 hours. The mixture was filtered and the filtrate was concentrated. Recrystallization of the crystalline residue from ethyl acetate-hexane gave 3.32 g (92%) of the product as white crystals, mp 129.5°–131.5° C.

(4) Preparation of N-benzoyl-N-(3-tert-butoxycarbonylaminophenyl)-glycine.

To a stirred solution of 1.3 g (3.3 mmol) of ethyl N-benzoyl N-(3-benzyloxycarbonylaminophenyl) glycinate in 15 ml of methanol was added 2.5 ml (7.5 mmol) of 3N sodium hydroxide. The mixture was stirred at 25° C. for 16 hours, then the methanol solvent was distilled off. The resulting solution was adjusted to pH 3 with 5N hydrochloric acid and the resulting mixture was extracted with ethyl acetate. The extracts were dried ($Na_2SO_4$) and concentrated to give a solid residue. Recrystallization of the solid from

EXAMPLE 8

5-[2-(tert-butoxycarbonylaminomethyl)phenyl]-2,4-pentadienoic acid

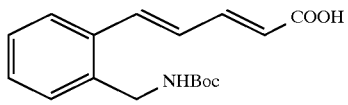

(1) Preparation of 1-azidomethyl-2-bromobenzene.

A mixture of 1-bromomethyl-2-bromobenzene (30 g, 120 mmol) and sodium azide (15.6 g, 240 mmol) in DMF (300 mL) was stirred at room temperature for 20 hours. The reaction mixture was poured into $H_2O$ (500 mL) and extracted with ethyl acetate (5×50 mL). The organic extracts were washed with water (3×50 mL), saturated sodium chloride (1×50 mL), dried over $Na_2SO_4$, filtered and the solvent removed in vacuo to give the product as an oil. Yield 24.87 g (97.8%).

(2) Preparation of 1-(tert-butoxycarbonylaminomethyl)-2-bromobenzene.

To a stirred solution of 1-azidomethyl-2-bromobenzene (24.87 g, 117.3 mmol) in THF (300 mL) and $H_2O$ (30 mL) was added triphenylphosphine (37.0 g, 141.0 mmol) portionwise. The mixture was stirred at room temperature for 18 hours and di-tert-butyl dicarbonate (33.3 g, 152.5 mmol) was added. The reaction mixture was stirred at room temperature for 1 hour, heated to reflux for 1 hour, cooled to room temperature and stirred for 2 hours. The solvent was removed in vacuo and the residue dissolved in a mixture of ether (200 mL) and $H_2O$ (200 mL). The layers were separated and the aqueous phase extracted with ether (4×50 mL). The organic extracts were washed with saturated sodium chloride (1×50 mL), dried over $Na_2SO_4$, filtered and the solvent removed in vacuo to give the crude product. Chromatography on silica gel, eluting with ethyl acetate-hexane (1 to 10% ethyl acetate, gradient) gave a white, crystalline solid. Yield 29.61 g (88.3%), mp 50°–53° C.

(3) Preparation of 5-[2-(tert-butoxycarbonylaminomethyl)phenyl]-2,4-pentadienoic acid methyl ester.

To a heavy walled Pyrex, Teflon screw-capped flask was added a solution of 1-(tert-butoxycarbonylaminomethyl)-2-bromobenzene (3.00 g, 10.5 mmol) in DMF (45 mL) under an argon atmosphere. To this was added triethylamine (4.5 mL, 32.25 mmol), methyl 1,3-butadiene-1-carboxylate (Fluka, 1.82 mL, 15.7 mmol), and $Pd(Ph_3P)_2Cl_2$ (Aldrich, 0.20 g, 0.28 mmol). The flask was sealed and heated at 100° C. for 40 hours. After cooling to room temperature the reaction mixture was diluted with ether (50 mL) and $H_2O$ (150 mL). The layers were separated and the aqueous phase extracted with ether (3×50 mL). The combined organic extracts were washed with $H_2O$ (5×25 mL), saturated sodium chloride (1×25 mL) and dried over $Na_2SO_4$. After filtration and removal of the solvent in vacuo, the residue was chromatographed on silica gel, eluting with ethyl acetate-hexane (5 to 10% ethyl acetate, gradient) to give first recovered starting material (1.60 g, 53.3%) and upon further elution the product as a white crystalline solid. Recrystallization from 1:3 ether/hexane gave white needles. Yield 0.89 g (26.7%; 57.3% based on recovered starting material), mp 96°–97.5° C.

(4) Preparation of 5-[2-(tert-butoxycarbonylaminomethyl)phenyl]-2,4-pentadienoic acid.

A mixture of 5-[2-(tert-butoxycarbonylaminomethyl)phenyl]-2,4-pentadienoic acid methyl ester (0.85 g, 2.68 mmol), $Na_2CO_3$ (1.17 g, 11.0 mmol), methanol (15 mL) and $H_2O$ (15 mL) was heated to reflux for 2 hours and cooled to room temperature. The methanol was removed in vacuo and the resulting aqueous solution diluted with $H_2O$ (50 mL), cooled to 0° C. and carefully acidifed with 1M hydrochloric acid. After extracting with $CH_2Cl_2$ (5×20 mL), these organic extracts were washed with saturated aqueous sodium chloride (1×25 mL), dried over $Na_2SO_4$, filtered and the solvent removed in vacuo. The residue was recrystallized from 1:3 $CH_2Cl_2$/hexane. Yield 0.70 g (86.2%), mp 179°–182° C.

EXAMPLE 9

$B_2$ Receptor Antagonist Compound Synthesis

The compounds indicated in Table I were synthesized manually using standard solid phase methods and t-Boc chemistry.

1. Boc-Arg(Tos)-PAM resin was used for the purpose. Amino acids and the Boc-protected derivatives of hydrophobic organic moieties (Y) prepared as described in Schemes 1 through XIV or in Examples 1 through 7 or taught in co-owned, co-pending patent applications were introduced according to the sequence of the compound.

2. Deprotection: The N-terminal t-Boc protection was accomplished by treating the resin-aa/resin-peptide with trifluoroacetic acid/methylene chloride (1:1) for two minutes followed by a similar treatment for 30 minutes.

3. The resin was then washed with methylene chloride and ethanol and neutralized with 10% triethylamine/methylene chloride or 10% diisopropylethylamine/methylene chloride.

4. Couplings: All couplings were carried out using the active ester of the amino acid. The active esters of the individual amino acids were generated prior to their introduction into solid phase synthesis. Five equivalents (with respect to loading of the first amino acid on the resin) of the amino acid, hydroxybenzotriazole hydrate and dicyclohexylcarbodiimide or diisopropylcarbodiimide, was incubated for 30 minutes at 0° C. in dimethylformamide or methylene chloride/dimethylformamide (1:1) for this purpose. Couplings were followed until no more free amine was detected on the resin using qualitative ninhydrin analysis (Kaiser test). Different unnatural amino acids behave differently during ninhydrin analysis and the color of the resin (after deprotection and coupling) depends on the specific amino acid being used.

5. After coupling, the resin-peptide was washed with dimethyl formamide and methylene chloride before commencement of another cycle of the synthesis.

6. The finished peptidyl-resin was cleaved from the resin using HF (10 mL/g of resin) in the presence of 10% anisole (scavenger). After removal of HF, the peptide resin was washed with ether and the peptide was extracted with 0.1% TFA or 0.2% acetic acid. Lyophilization yielded crude peptide, usually flaky yellow solids were obtained at this stage.

7. The crude peptide was purified using reverse phase high performance liquid chromatography on a $C_{18}$ column using a gradient of water/acetonitrile (both containing 0.1% trifluoroacetic acid or 0.2% acetic acid). The pure fractions were determined by analytical HPLC, on a Vydac $C_{18}$ column using a gradient of water/acetonitrile (both containing 0.1% trifluoroacetic acid) and pooled together and lyophilized to give flaky white solids.

8. Peptides were analyzed by analytical reverse phase HPLC on a Vydac $C_{18}$ column using a gradient of water/acetonitrile (both containing 0.1% trifluoroacetic acid), and fast atom bombardment mass spectroscopy.

EXAMPLE 10

$B_1$ Receptor Antagonist Compound Synthesis

The $B_1$ receptor antagonists corresponding to the compounds prepared in Example 9, wherein the C-terminal arginine is deleted, are prepared in an analogous manner. The solid phase synthesis is initiated using Boc-Oic-PAM resin obtainable from a commercial supplier (Advanced Chemtech, Louisville, Ky.).

EXAMPLE 11

Bradykinin Binding Procedures

Guinea Pig Ileum Binding

Binding of $^3$H-bradykinin was performed using the method of D. C. Manning, R. Vavrek, J. M. Stewart, and S. H. Snyder, *J. Pharmacol. Exp. Ther.*, (1986) 237:504. The tissues used in the binding assay were terminal ileum from male Hartley guinea pigs (150–350 g). After dissection, tissues were placed in 20 volume of ice-cold buffer A (25 mM TES containing 0.2 g/l of 1,10-phenanthroline adjusted of pH 6.8 with ammonium hydroxide) and homogenized using a Polytron Tissumizer at setting 6 for 15 seconds. The homogenate was centrifuged at 50,000×g for 10 minutes, the supernatant discarded, and the pellet resuspended in ice-cold buffer A by homogenization with the Polytron. Each tissue was homogenized and centrifuged three times. The final pellet was resuspended in buffer A containing bovine serum albumin (1 g/l) and Bacitracin (0.14 g/l) to a final volume of 170 ml/g of the original tissue weight. The binding assay consisted of 1 mM in 12×75 mm polypropylene tubes: 50 $\mu$l $^3$H-bradykinin (20,000 dpm, ~0.3 nM in the final assay volume), 100 $\mu$l displacing drug in buffer A, and 750 $\mu$l tissue homogenate. Each tray contained tubes, to which no drug was added to measure maximum binding and tubes to which bradykinin (1 $\mu$M final concentration) had been added, to measure specific binding. Specific binding accounted for 96–98% total binding. Tubes were incubated for 90 minutes at ambient temperature. The assays were terminated by filtration over Whatman GF/B glass fiber filters that had been pretreated for 2 hours with polyethyleneimine (2 g/l) using a Brandel Tissue Harvester, followed by washing with 4×1 ml aliquots of ice-cold 50 mM Tris, pH 7.4. Filters were dissolved in Ready-Safe Fluor (Beckman) for at least 90 minutes before quantitation by liquid scintillation spectrometry. $K_d$ values were determined using saturation binding and analysis by EBDA (G. A. MacPherson, *J. Pharmacol. Methods* (1985) 213), followed by LIGAND (P. J. Munson, D. Rodbard, *Anal. Biochem.* (1980) 220). $K_i$ values were determined using competitive analysis followed by EBDA and LIGAND.

Human Bradykinin Receptor Binding

The human bradykinin $B_2$ receptor was cloned by Hess et al. (*Biochem. Biophys. Res. Comm.* (1992) 184:260–268). A human bradykinin $B_2$ receptor was expressed in CHO/K cells. Briefly, approximately $2\times10^6$ plaques from a human uterus λgt10 cDNA library (Clontech Laboratories; Palo Alto, Calif.) were screened using a PCR fragment containing the coding region of the rat $B_2$ receptor. This probe was generated by random-primed synthesis in the presence of $\alpha[^{32}P]$dATP. Duplicate filters were hybridized overnight at 42° C. in 1M NaCl, 50 mM Tris pH 7.5, 5× Denhardt's, 200 $\mu$g/ml salmon sperm DNA, 1% SDS, and 20% formamide. The filters were washed at 65° C. in 1× SSC and 1% SDS. Coincident positively hybridizing plaques were purified and rescreened with the same probe and stringency conditions. EcoRI fragments of positive clones were inserted into Bluescript/KS II+vector (Stratagene; La Jolla, Calif.) for sequence determination.

The nucleotide sequence of the cloned human $B_2$ receptors was determined using double-stranded DNA and the dideoxy chain termination method. Commercially available T3 and T7 oligonucleotides (USB; Cleveland, Ohio) and synthetic 21-mer oligonucleotides (DNA/RNA Synthesizer; applied Biosystems Inc.; Palo Alto, Calif.) from both the known rat sequence and the determined human sequence were used to identify the nucleotide sequence from the 5' untranslated end to the BglII site in the 3' untranslated end of the clone. The HindIII/XbaI fragment of one full-length clone, 126A, was inserted into pcDNAI neo vector (Invitrogen; San Diego, Calif.) for expression in mammalian cell lines.

CHO/K cells were plated in 2 ml of growth medium (Ham's F12 with 10% FBS) per 6 well plate and incubated at 37° C., 5% $CO_2$ until they were 60% confluent. For each well, 4, 12, and 16 $\mu$g of DNA was diluted in 100 $\mu$l Opti-MEM I reduced serum medium (Gibco/BRL; Gaithersburg, Md.). 12 $\mu$l of TransfectASE reagent (Gibco/BRL) was diluted in a separate aliquot of 100 $\mu$l Opti-MEM I. The DNA and TransfecASE solutions were combined, mixed gently, and incubated at 25° C. for 15 minutes. This solution was then diluted to 1 ml with Opti-MEM I. Each well was washed twice with Opti-MEM I and 1 ml of the DNA/TransfectAse complex was added to each well. After a 5 hour incubation at 37° C. and 5% $CO_2$, 1 ml of Ham's F12 with 20% FBS was added to each well and cells were incubated overnight. Media was replaced with growth medium and incubated for additional 24 hours.

Cells were harvested by trypsinization and replated in selection medium (Ham's F12, 10% FBS and 500 $\mu$g/ml Geneticin (Gibco/BRL). Media was replaced every 48 hours for 2 weeks. Any colonies remaining after selection were transferred to separate 10 cm dishes, grown to confluency and positive clones were determined by binding of $^3$H-NPC17731 a bradykinin antagonist peptide described by Burch et al. (DuPont Biotech update (1992) 4:127–140). Colonies expressing the receptor were put out at limiting dilution. Cells were expanded and positive clones were identified as above. A cell line designated H2O.2 was used to quantitate binding of the compounds of the invention to the human bradykinin $B_2$ receptor.

Radioligand Binding Assays

This assay measures the ability of a bradykinin antagonist compound to compete for binding to the human $B_2$ receptor with tritiated bradykinin or tritiated NPC17731, a bradykinin analog which is known to bind the $B_2$ receptor and act as a bradykinin antagonist.

H2O.2 cells were grown to confluency in Ham's F12 media containing 10% FBS and 500 $\mu$g/ml Geneticin. Growth media was aspirated and the monolayer washed once with Dulbecco's PBS without $Ca^{++}$ and $Mg^{++}$. Cells were scraped in Dulbecco's PBS and centrifuged at 2,000×g for 10 minutes. Pellets were resuspended in 25 mM TES, 1 mM 1,10-phenanthroline pH 6.8 buffer and homogenized using a Ploytron at setting 5 for 10 seconds. An aliquot was taken for a protein determination using a BioRad protein assay kit. Membranes were centrifuged at 48,000×g for 10 minutes at 4° C. Pellets were resuspended in the TES buffer with 0.1% BSA and 0.014% bacitracin. 0.5 ml aliquots were frozen in liquid $N_2$ and stored at −80° C. for up to 2 weeks.

Membranes from H2O.2 cells previously prepared were thawed at 37° C. and diluted in 25 mM TES, 1 $\mu$M 1,10-phenanthroline pH 6.8 containing BSA and bactiracin. For saturation binding assays, increasing concentrations of $^3$H-bradykinin ($^3$HBK) or $^3$H-NPC17731 (a known bradykinin antagonist which binds the B$_2$ receptor and which has the amino acid sequence)were incubated with 16.5 μg of membrane protein in a total volume of 3 ml of the same buffer. Non-specific binding was determined with 1 μM bradykinin. The tubes were incubated 90 minutes at 25° C. and the assay was terminated by rapid vacuum filtration onto Whatman GF/B filters presoaked with 0.2% PEI for 3 hours followed by 2×3 ml aliquots of ice-cold 50 mM Tris, pH 7.4. Radioactivity was counted with a Beckman scintillation counter.

Whole Cell Binding Assay

Binding to confluent monolayers of transfected cells expressing the human B$_2$ receptor (7,000 fmol/receptor/mg) grown in 24-well plates was measured by incubating cells in 1 ml cell binding buffer (PBS/Ca/Mg, 1% BSA, 0.14 mg/ml bacitracin) containing 10$^{-10}$M $^3$H-bradykinin and various concentrations of unlabeled analogs for 4 to 10 hours at 4° C. Cells were washed three times with cell binding buffer and lysed in 0.1N NaOH. An aliquot of the lysate was counted to measure radioactivity bound.

EXAMPLE 12

Guinea Pig-Ileum Contraction Assay

Guinea pig intestine was removed and placed in a Petri dish containing Tyrodes solution and cut into 3–4 cm segments. The longitudinal muscle was separated from the underlying circular muscle using a cotton applicator (Paton and Zar, *J. Physiol.* (1968) 194:13. Muscle strips were connected to isometric force-displacement transducers (Grass or Gould) coupled to a physiograph and placed in tissue baths containing Tyrode's solution at 37° C. Each preparation was suspended under a resting tension of 2 g.

After equilibration of the tissues, appropriate volumes of bradykinin solutions were cumulatively added to the 10 ml tissue baths to increase the concentration of bradykinin in the bath step-by-step without washing out after each single dose. Higher concentrations were added only after the preceding contraction had reached a steady value. When the next concentration step did not cause a further increase in contraction, it was assumed that the maximum effect had been obtained and the tissue was washed to remove bradykinin and allowed to recover for 15 minutes. Antagonism of bradykinin responses to the presence of antagonist were determined by repeating the cumulative addition procedure for bradykinin after the tissue has been exposed to the antagonist for 5 minutes. Three or four different concentrations of antagonist were studied sequentially in the same preparations. Responses were expressed as a percentage of the maximum concentration elicited by bradykinin in the absence of antagonist. pA$_2$ values were calculated by Schild analysis.

Assay Results

Table I lists results obtained in the various assays described above for a variety of bradykinin antagonist compounds of the invention. In addition the atomic volume, in cubic angstroms, has been calculated for the Y moieties of a number of the compounds, according to the previously described method of Pearlstein, and is given in Table I.

TABLE 1

| COMPOUND | Radioligand Binding | | | Guinea Pig Ileum Contraction $pA_2$ | Atomic Volume $Å^3$ |
|---|---|---|---|---|---|
| | Whole Cell $^3$HBK | Human $^3$HBK | Human $^3$H17731 | Guinea Pig | |
| H—D—Arg—Arg—NH—[crotonyl]—Ser—D—Tic—Oic—Arg—OH | | | 229 | | |
| H—D—Arg—Arg—NH—CH$_2$—[2-cinnamoyl-phenyl]—Ser—D—Tic—Oic—Arg—OH | | | 27 | 120 ± 8 | |
| H—D—Arg—Arg—NH—CH$_2$—[2-cinnamoyl-phenyl]—Ala—D—Tic—Oic—Arg—OH | | | | 278 ± 56 | |
| H—D—Arg—Arg—NH—CH$_2$—[2-(3-phenylpropanoyl)-phenyl]—Ser—D—Tic—Oic—Arg—OH | | | | 563 ± 146 | |
| H—D—Arg—Arg—NH—CH$_2$—[3-cinnamoyl-phenyl]—Ser—D—Tic—Oic—Arg—OH | | | | 496 ± 92 | |

TABLE 1-continued

| COMPOUND | Radioligand Binding | | | Guinea Pig Ileum Contraction $pA_2$ | Atomic Volume $Å^3$ |
|---|---|---|---|---|---|
| | Whole Cell $^3$HBK | Human $^3$HBK | Human $^3$H17731 | Guinea Pig | |
| H—D—Arg—Arg—Arg—NH—CH₂—(3-phenyl)—CH₂CH₂—C(O)—Ser—D—Tic—Oic—Arg—OH | | | | 466 ± 73 | |
| H—D—Arg—Arg—Arg—NH—CH₂—(2-phenyl)—CH=CH—CH₂—C(O)—Ser—D—Tic—Oic—Arg—OH | | 51 | 17 | | 6.10 |
| H—D—Arg—Arg—Arg—NH—CH₂CH₂—(2-phenyl)—CH=CH—C(O)—Ser—D—Tic—Oic—Arg—OH | | | 23 | | |
| H—D—Arg—Arg—Arg—NH—CH₂—(cyclohexyl)—CH=CH—C(O)—Ser—D—Tic—Oic—Arg—OH | | | | 638 ± 84 | |
| H—D—Arg—Arg—Pro—N(pyrrolidine)—CH=CH—CH₂—C(O)—Phe—Ser—D-Hype(trans-thiophenyl)-Oic—Arg—OH | | | 15 | 174 | |
| H—D—Arg—Arg—N(pyrrolidine)—CH=CH—(CH₂)₄—CH=CH—C(O)—Ser—D-Hype(trans-thiophenyl)-Oic—Arg—OH | | | | 2123 | |

TABLE 1-continued

| COMPOUND | Radioligand Binding | | | Guinea Pig Ileum Contraction pA$_2$ | Atomic Volume Å$^3$ |
| --- | --- | --- | --- | --- | --- |
| | Whole Cell $^3$HBK | Human $^3$HBK | Human $^3$H1773I | Guinea Pig | |
| H—D—Arg—Arg—Pro—N[cyclopentyl-CH=CH-(CH$_2$)$_n$-C(O)]—Ser—D-Hype(trans-thiophenyl)-Oic—Arg—OH | | | | 1896 | |
| H—D—Arg—Arg—N[cyclopentyl-CH=CH-(CH$_2$)$_n$-CH(CH$_2$Ph)-C(O)]—Ser—D—Tic—Oic—Arg—OH | | | | 400 | |
| H—D—Arg—Arg—Pro—Hyp—N[H, CH$_2$-CH=CH-CH(CH$_2$Ph)-C(O)]—Ser—D—Tic—Oic—Arg—OH | | | 21 | 358 | |
| H—D—Arg—Arg—N[cyclopentyl-CH=CH-(CH$_2$)$_n$-CH(CH$_2$Ph)-C(O)]—Ser—D—Tic—Oic—Arg—OH | | | | | |
| H—D—Arg—Arg—NH—[CH$_2$-C$_6$H$_4$-CH=CH-C(O)]—Phe—Ser—D—Tic—Oic—Arg—OH | | | | 1267 ± 173 | |

TABLE 1-continued

| COMPOUND | Whole Cell ³HBK | Human ³HBK | Human ³H17731 | Guinea Pig | Guinea Pig Ileum Contraction pA₂ | Atomic Volume Å³ |
|---|---|---|---|---|---|---|
| H—D—Arg—Arg—NH—[2-(N-benzyl-Gly-Ser-D-Tic-Oic-Arg-OH)cinnamoyl structure] | | | 28 | | | |
| H—D—Arg—Arg—X[Ph]—CH₂CO—Ser—D—Tic—Oic—Arg—OH | | | 7.7 | | 6.7 | |
| H—D—Arg—Arg—X[4-CH₃Ph]—CH2CO—Ser—D—Tic—Oic—Arg—OH | | | 6.3 | | | |
| H—D—Arg—Arg—X[c-C₆H₁₁CH2]—CH₂CO—Ser—D—Tic—Oic—Arg—OH | | | 6.8 | | 6.4 | |
| H—D—Arg—Arg—X[c-C₆H₁₁]—CH₂CO—Ser—D—Tic—Oic—Arg—OH | | | 0.73 | | | |
| H—D—Arg—Arg—X[n-Pr]—CH₂CO—Ser—D—Tic—Oic—Arg—OH | | | 5.80 | | | |
| H—D—Arg—Arg—X[4-CH₃OPh]—CH₂CO—Ser—D—Tic—Oic—Arg—OH | | | — | | | |
| H—D—Arg—Arg—X[Ph]—CH₂CO—Ala—D—Tic—Oic—Arg—OH | | | 18.6 | | | |
| H—D—Arg—Arg—X[Ph]—CH₂CO—Gly—D—Tic—Oic—Arg—OH | | | 66 | | | |
| H—D—Arg—Arg—X[Ph]—CH₂CO—N—BnGly—D—Tic—Oic—Arg—OH | | | 54 | | | |
| H—D—Arg—Arg—X[Ph]—CH₂CO—N—BnGly—Ser—D—Tic—Oic—Arg—OH | | | 31 | | | |
| H—D—Arg—Arg—X[Ph]—CH₂CO—D—Tic—Oic—Arg—OH | | | 111 | | | |
| H—D—Arg—Arg—X[Ph]—(CH₂)₄CO—D—Tic—Oic—Arg—OH [tetrahydro-β-carboline structure with DArg-Arg-N, Ser-DTic-Oic-Arg] | 59 | | | | | 223.8 |
| [benzimidazolone-piperidine structure with DArg-Arg-N, Ser-DTic-Oic-Arg] | | | 58 | | | 259.5 |

TABLE 1-continued

| COMPOUND | Radioligand Binding | | | Guinea Pig Ileum Contraction $pA_2$ | Atomic Volume $Å^3$ |
|---|---|---|---|---|---|
| | Whole Cell $^3$HBK | Human $^3$HBK | Human $^3$H1773I | Guinea Pig | | |
| DArg-Arg-[structure]-Ser-DTic-Oic-Arg | | | 78 | | 223.8 |
| DArg-Arg-[structure]-Ser-DTic-Oic-Arg | | | 3.3 | | 233.6 |
| DArg-Arg-[structure]-Ser-DTic-Oic-Arg | | | 27 | | 152.6 |

TABLE 1-continued

| COMPOUND | Radioligand Binding | | | Guinea Pig Ileum Contraction pA$_2$ | Atomic Volume Å$^3$ |
|---|---|---|---|---|---|
| | Whole Cell $^3$HBK | Human $^3$HBK | Human $^3$H17731 | Guinea Pig | | |

| COMPOUND | Whole Cell $^3$HBK | Human $^3$HBK | Human $^3$H17731 | Guinea Pig | Contraction pA$_2$ | Volume Å$^3$ |
|---|---|---|---|---|---|---|
| DArg—Arg—N⟨piperidine-phenyl⟩—C(O)—CH$_2$—N⟨morpholine⟩—C(O)—Ser—DTic—Oic—Arg | | 7.8 | | | 6.7 | 266.4 |
| DArg—Arg—NH—(CH$_2$)$_{11}$—C(O)—Ser—DTic—Oic—Arg | | | 31 | | 5.6 | 223.3 |
| DArg—Arg—NH—(CH$_2$)$_5$—C(O)—Ser—DTic—Oic—Arg | | | 100 | | | 134.9 |

EXAMPLE 13

Preparation of bradykinin antagonists incorporating novel beta turn mimetics

Following deprotection of the Boc-Arg(Tos)-PAM resin in the procedure of Example 9, sequential coupling of the appropriate amino-protected acids were carried out using previously described solid phase peptide synthesis chemistry to obtain the following bradykinin antagonist compounds.

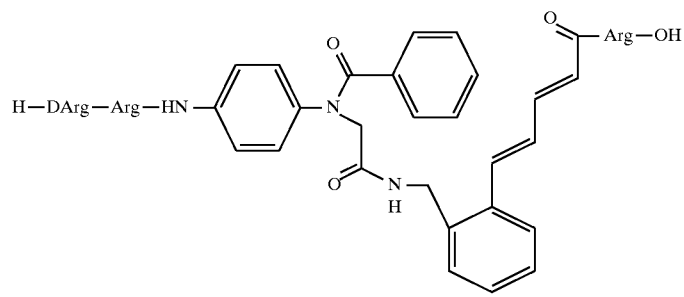

(1)

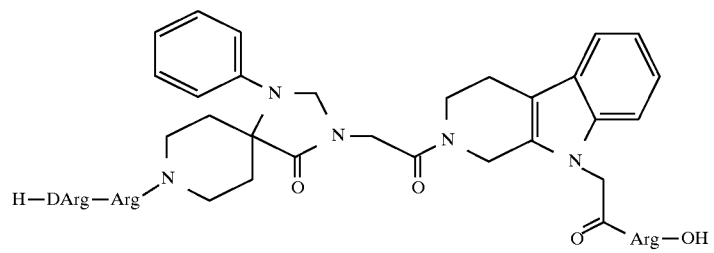

(2)

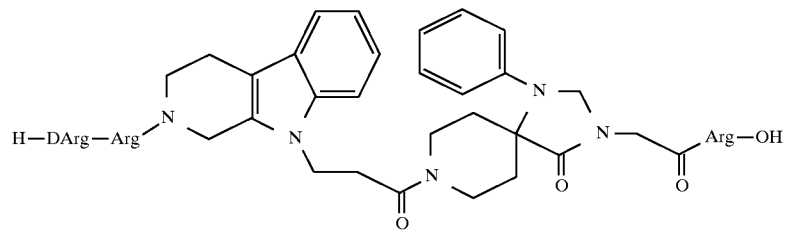

(3)

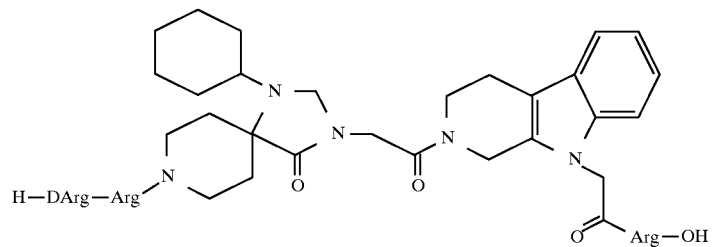

(4)

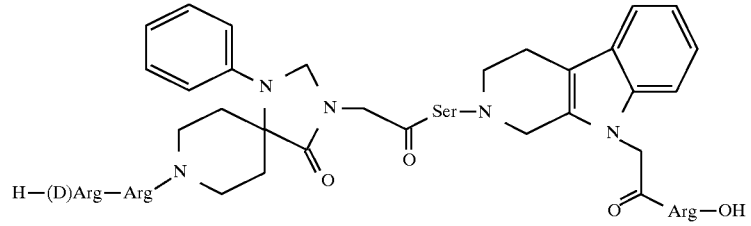

(5)

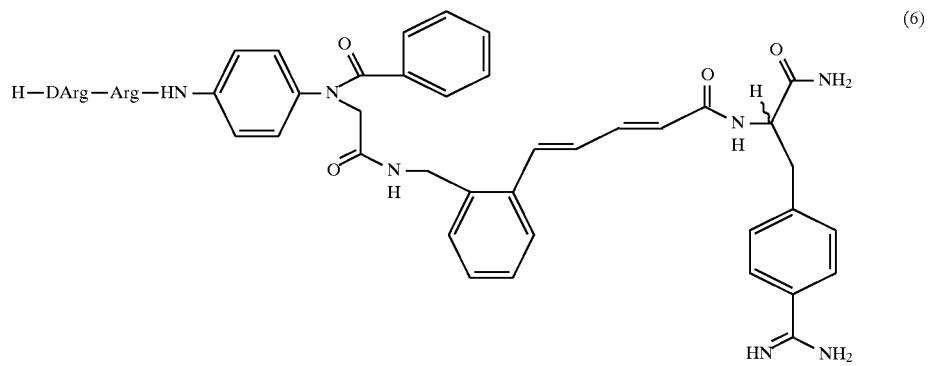
(6)
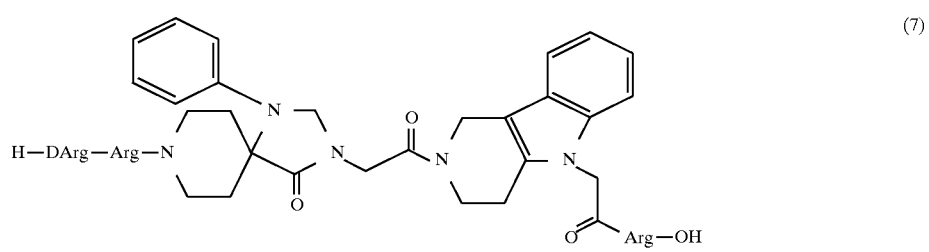
(7)
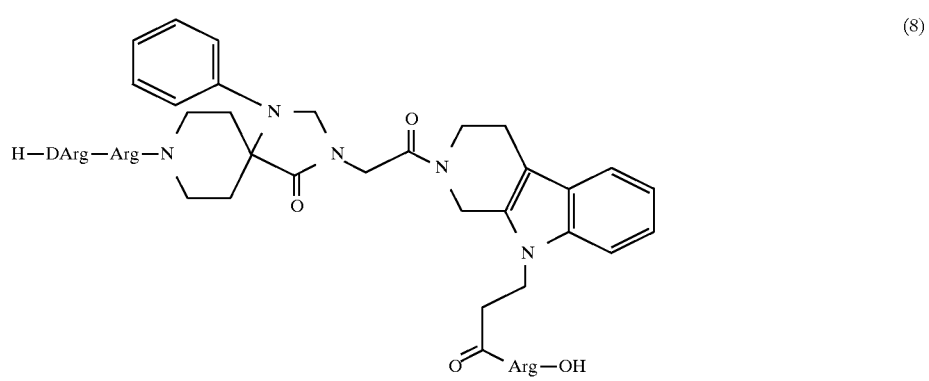
(8)
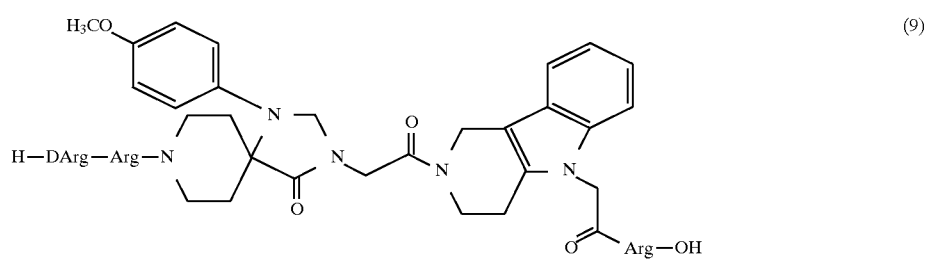
(9)
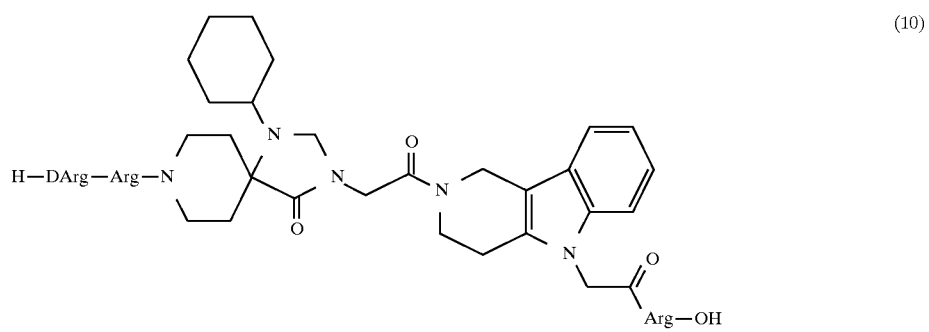
(10)

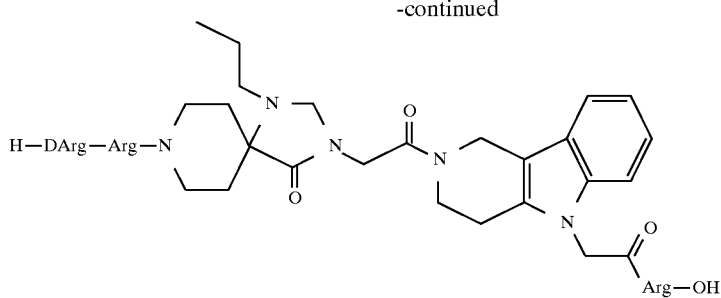

(11)

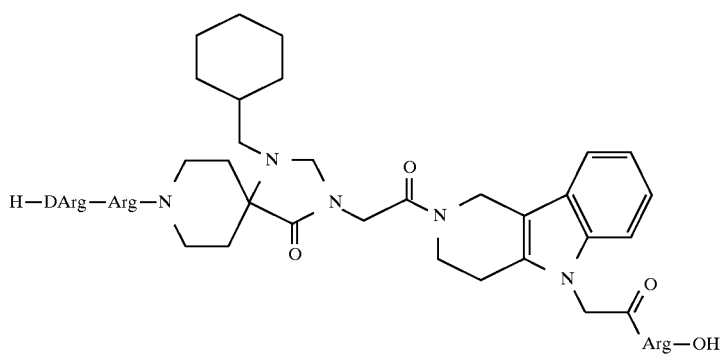

(12)

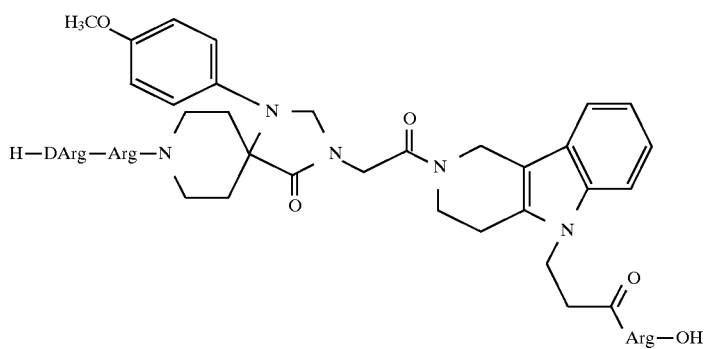

(13)

EXAMPLE 14

Preparation of bradykinin antagonists incorporating novel beta turn mimetics and ariginine mimetics The appropriate Boc-protected amino acid corresponding to the desired arginine mimetics were treated with hydroxybenzotriazole hydrate (1 equivalent) and di-isoproylcarbodiimide in methylene chloride:dimethyl formamide (1:1) at 0° C. for 30 min to form an active ester of the Boc amino acid. The active ester was then shaken with p-methoxybenzhydryamine resin until no further amine was detected on the resin by Kaiser test. The loading of the non-natural amino acid was taken to be equal to the initial amine content on the p-methoxybenzhydryamine resin. Following deprotection of the arginine mimetic, sequential coupling of appropriate acids, using the solid phase synthesis procedure of Example 9, was carried out to synthesize the desired pseudopeptide. Cleavage of the pseudopeptide from the resin with HF yielded the compound as an amide. In this manner, the following compounds were prepared.

(14)
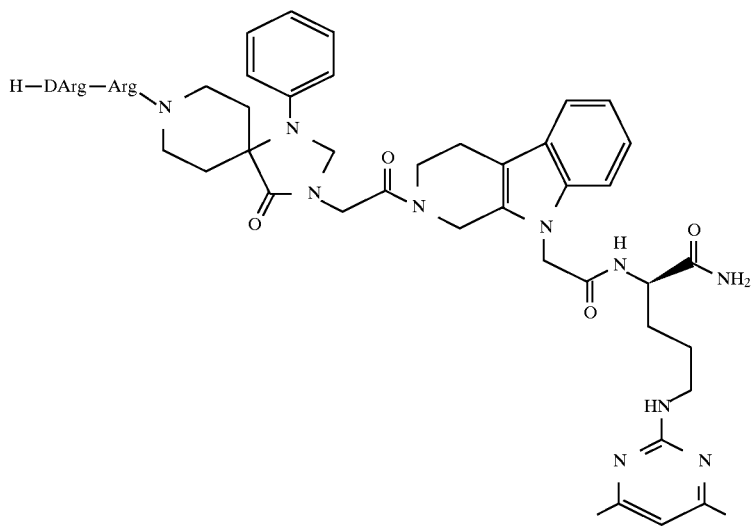
(15)
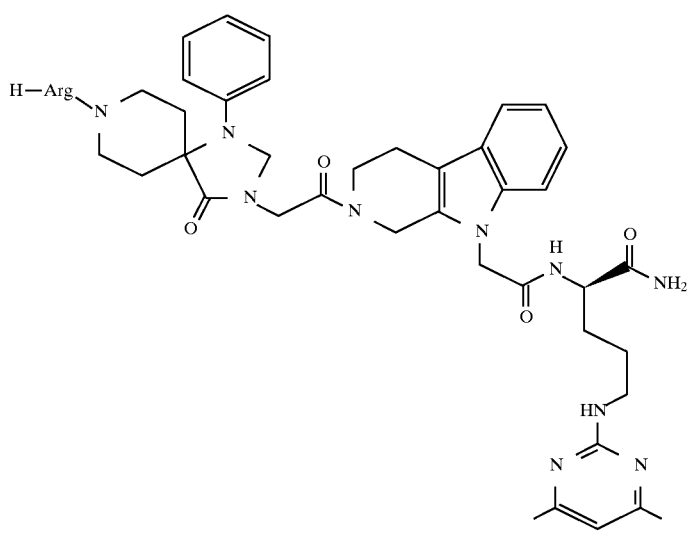
(16)
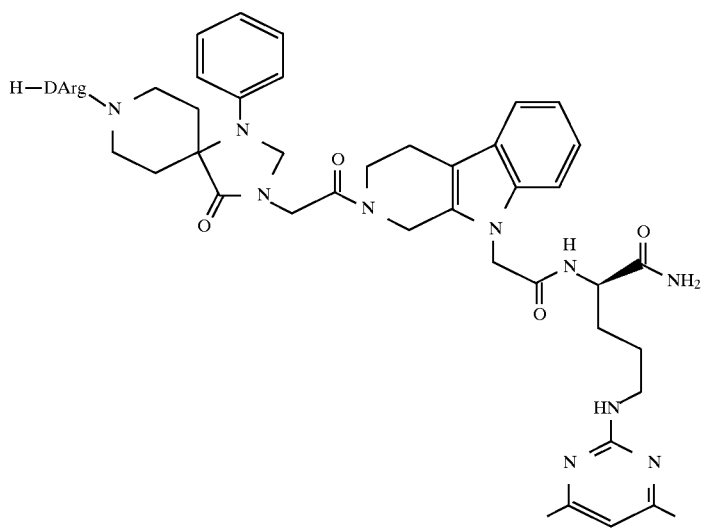

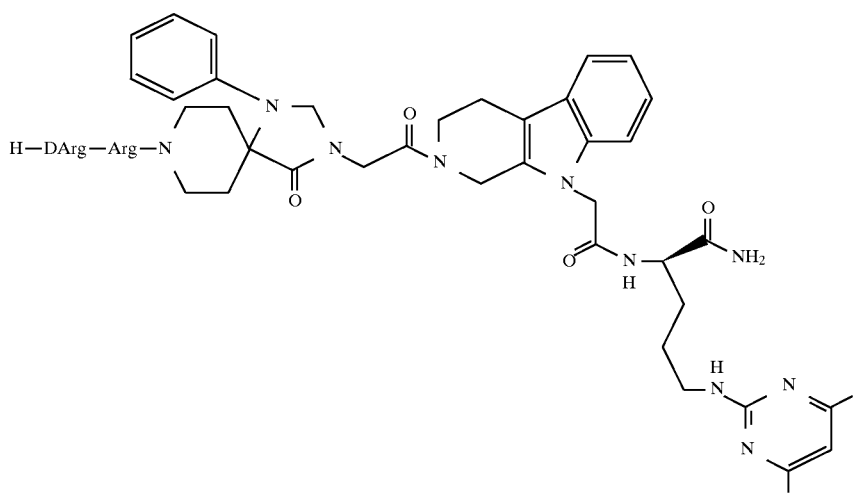
(17)
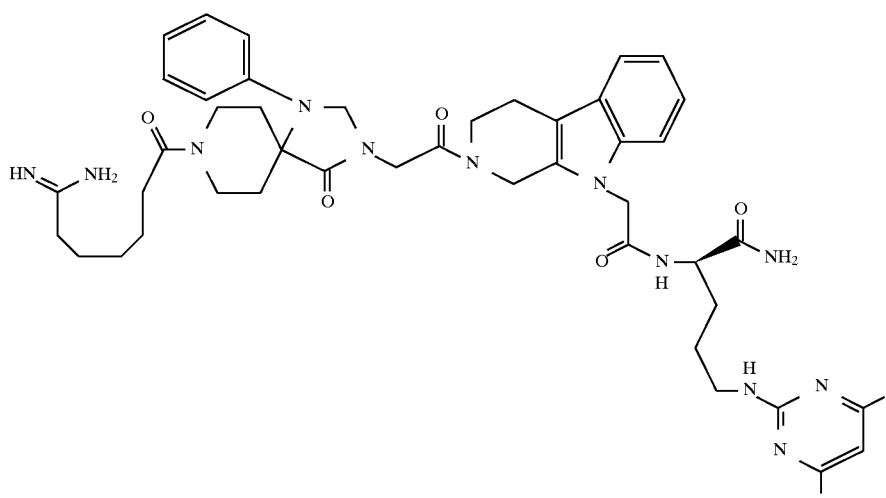
(18)
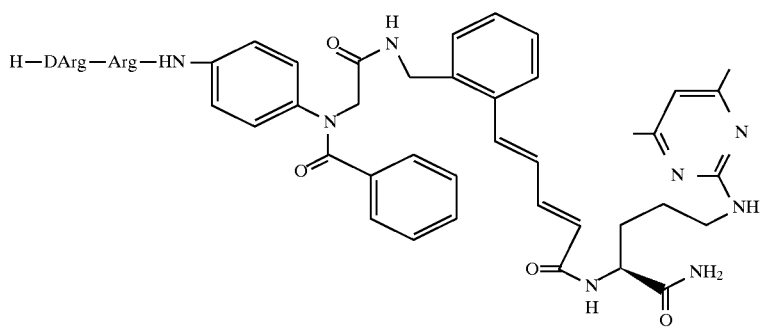
(19)

-continued (20)

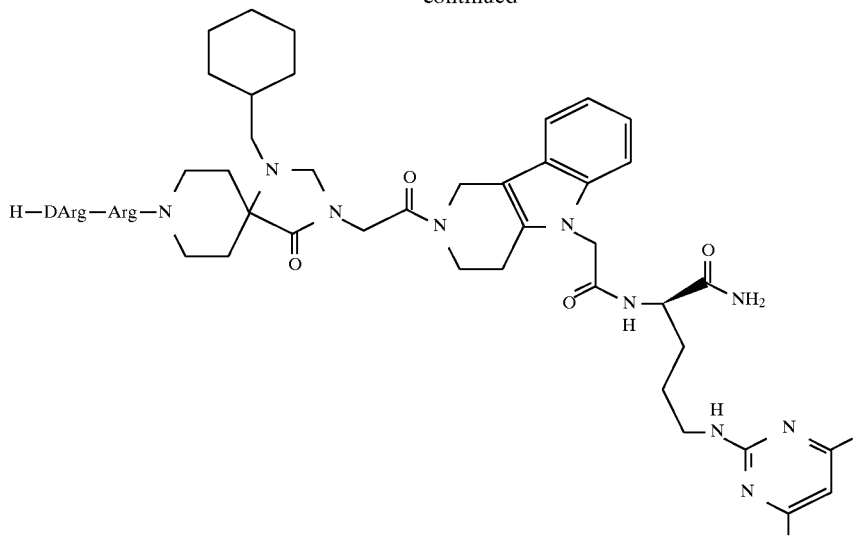

Bradykinin $B_1$ receptor antagonists corresponding to the compounds of Example 13 and Example 14 can be prepared by coupling the acid corresponding to the beta turn mimetic directly to the resin to initiate solid phase synthesis.

EXAMPLE 15

Competitive binding assays of compounds incorporating novel beta turn mimetics

The ability of the compounds of Example 13 and Example 14 to competitively bind the human $B_2$ bradykinin receptor was assayed using previously described procedures. The results are presented in Table 2. In some cases, the results represent averages for a number of repeated assays.

TABLE 2

| | Radioligand Binding, Ki | | |
|---|---|---|---|
| Compound No. | Human $^3$H17731 (nM) | Human $^3$HBK (nM) | Whole Cell $^3$HBK (μM) |
| 1 | | 36 | 5.5 |
| 2 | 94 | 1800 | 10.4 |
| 3 | | 570 | |
| 4 | | 1400 | |
| 5 | | 466 | |
| 6 | | 83.8 | 0.6 |
| 7 | | 325 | |
| 8 | | 223 | |
| 9 | | 129 | |
| 10 | | 229 | |
| 11 | | 473 | |
| 12 | | 168 | |
| 13 | | 608 | |
| 14 | | 78.4 | |
| 15 | | 285 | |
| 16 | | 212 | |
| 17 | | 38.7 | |
| 18 | | 1870 | |
| 19 | | 19.3 | |
| 20 | | 52 | |

EXAMPLE 16

Determination of $B_1$ receptor antagonist activity

The ability of a pseudopeptide of the invention to antagonize $B_1$ receptor mediated inflammatory responses in vivo can be confirmed by testing the ability of the pseudopeptide to inhibit des $Arg^9$-bradykinin induced hypotension in rabbits that have been pretreated with lipopolysaccharides. It is known that, in the presence of inflammation-inducing substances, including lipopolysaccharide and interleukin-1, $B_1$ receptors are upregulated and respond to des $Arg^9$-bradykinin to produce inflammatory responses, including hypotension.

Male New Zealand white rabbits (1.5–2.0 kg) are pretreated with a freshly made solution of LPS (10 μg/100 ml) 5 hr prior to anesthetizing with sodium phenobarbital i.v. The left carotid artery is cannulated for recoding mean arterial blood pressure and the left jugular vein for des $Arg^9$-bradykinin (1 μg/kg) and the pseudopeptide to be tested. Animals are pulsed with a bolus of des $Arg^9$-bradykinin (3×) at 5 minute intervals to produce a basal hypotensive response. Test pseudopeptide is then administered as a bolus prior to des $Arg^9$-bradykinin and its ability to antagonize the $B_1$-mediated hypotensive response is determined as % inhibition.

We claim:

1. A compound having the formula

X-Y-Z wherein:

X is an arginine or lysine residue; or

X is a di- or tri-peptide wherein the constituent amino acids are selected from the group consisting of the L- and D-isomers of Arg, Gln, Asn, Lys, Sar, N-ε-acetyl-Lys, $N^G$-p-tosyl-Arg, $N^G$-nitro-Arg, N-α-acetyl-Arg and citrulline, with the proviso that at least one of the constituent amino acids is lysine or arginine;

Y is selected from the group consisting of

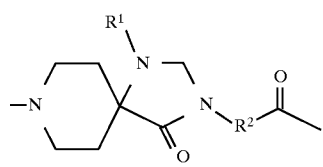

wherein $R^1$ is selected from the group consisting of a substituted or unsubstituted aryl group, a straight, branched, saturated or unsaturated lower alkyl chain of 1 to 6 carbon atoms and a cycloalkyl or alkylmethyl in which the cycloalkyl ring comprises 3 to 6 carbons and $R^2$ is a saturated or unsaturated alkylene bridging group consisting of 1 to 8 carbon atoms optionally substituted with a benzyl or naphthyl group;

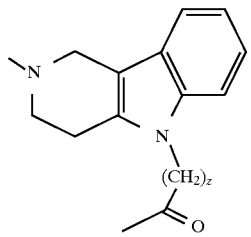

wherein z is an integer from 1 to 3;

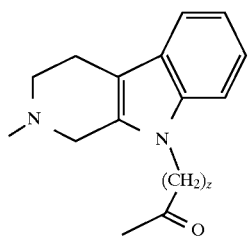

wherein z is an integer from 1 to 3; and

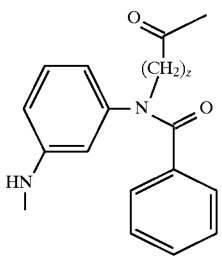

wherein z is an integer from 1 to 3; and

Z is a group of the formula

-E-β-H'-Cn wherein:
E is a direct bond or is selected from the group consisting of Ser, Gly and Val;
β is selected from the group consisting of

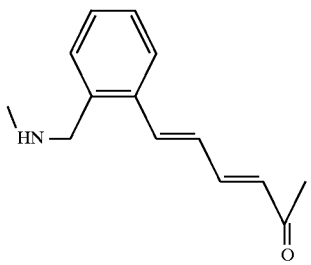

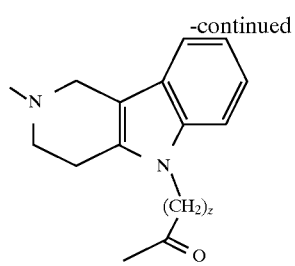

and

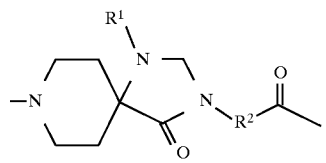

wherein z is an integer from 1 to 3, $R^1$ is selected from the group consisting of a substituted or unsubstituted aryl group, a straight, branched, saturated or unsaturated lower alkyl chain of 1 to 6 carbon atoms and a cycloalkyl or alkylmethyl in which the cycloalkyl ring comprises 3 to 6 carbons;

H' is selected from Arg,

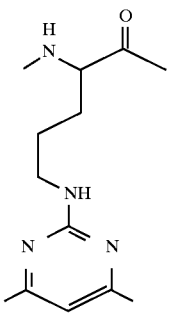

and

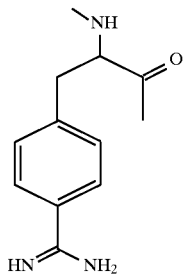

2. The compound of claim 1 wherein X is DArg-Arg.

3. The compound of claim 2 having the formula

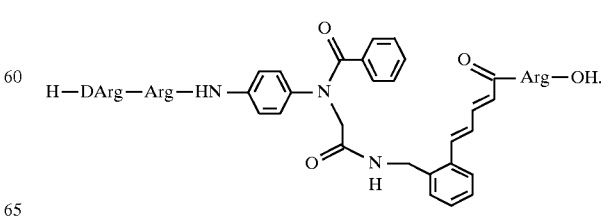

4. The compound of claim 2 having the formula

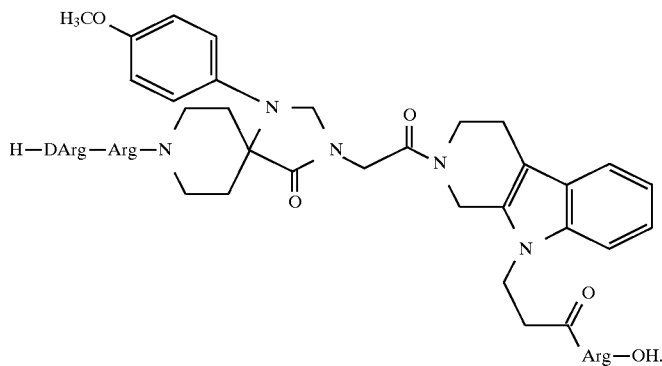
5. The compound of claim 2 having the formula
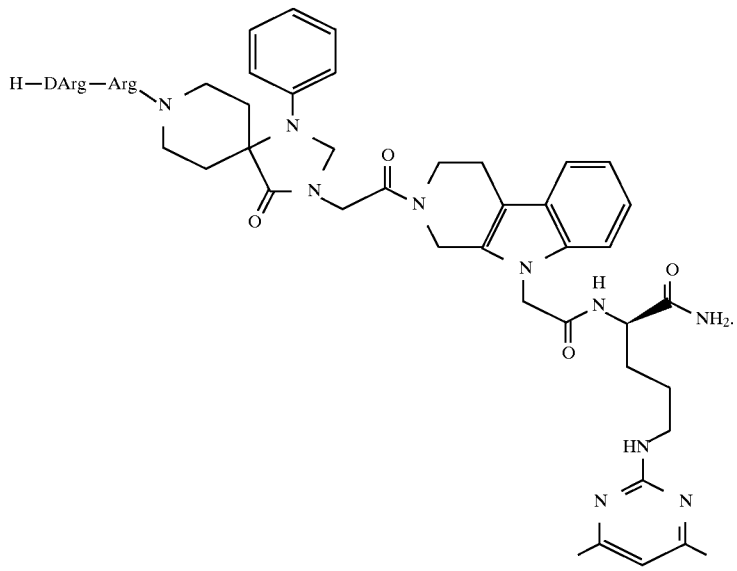
6. The compound of claim 2 having the formula
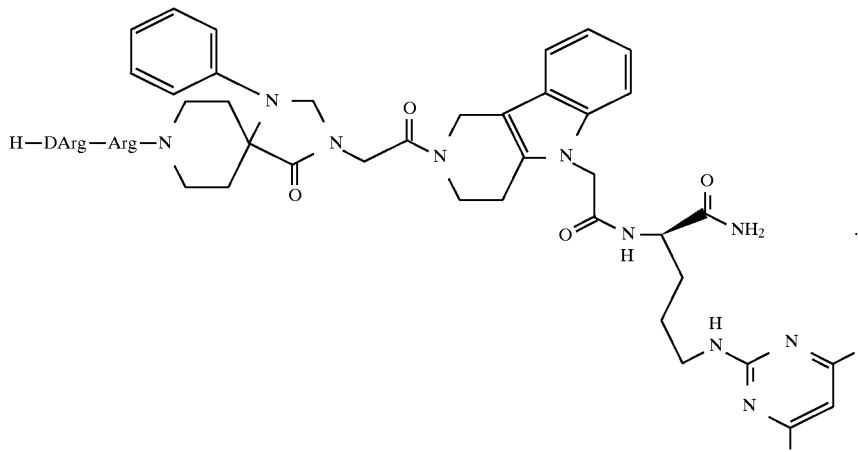
7. The compound of claim 2 having the formula

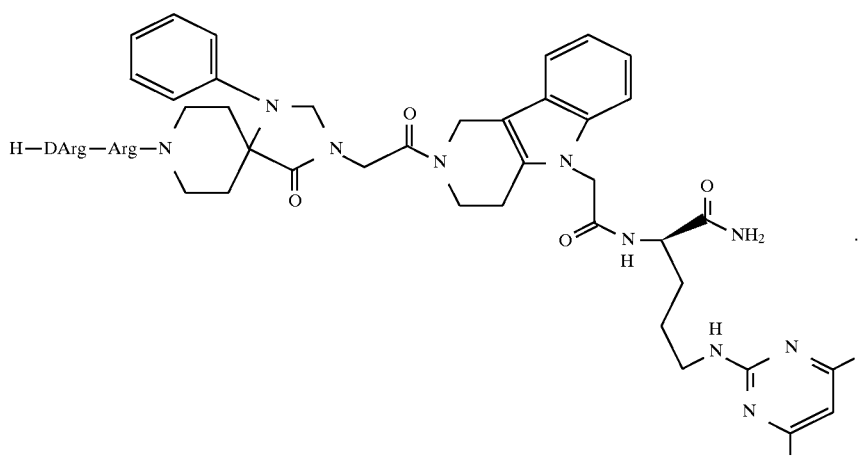
8. A method for treating an acute inflammatory condition mediated by bradykinin which comprises administering an effective amount of the compound of claim 2 to an animal in need of such treatment.
9. A method for antagonizing bradykinin $B_2$ receptor activity in a mammal which comprises administering to the mammal an effective amount of a compound of claim 1.
* * * * *